(12) United States Patent
Dodd et al.

(10) Patent No.: US 12,090,264 B2
(45) Date of Patent: Sep. 17, 2024

(54) APPARATUSES AND METHODS FOR WOUND THERAPY

(71) Applicant: Smith & Nephew PLC, Watford (GB)

(72) Inventors: James Roderick Dodd, Driffield (GB); Victoria Jody Hammond, Hull (GB); Edward Yerbury Hartwell, Hull (GB); John Kenneth Hicks, York (GB); Elizabeth Mary Huddleston, York (GB); Carl Saxby, Brough (GB)

(73) Assignee: Smith & Nephew PLC, Watford (GB)

( * ) Notice: Subject to any disclaimer, the term of this patent is extended or adjusted under 35 U.S.C. 154(b) by 397 days.

(21) Appl. No.: 17/478,403

(22) Filed: Sep. 17, 2021

(65) Prior Publication Data

US 2022/0071806 A1 Mar. 10, 2022

Related U.S. Application Data

(63) Continuation of application No. 16/105,852, filed on Aug. 20, 2018, now Pat. No. 11,123,226, which is a
(Continued)

(51) Int. Cl.
*A61M 1/00* (2006.01)
*A61B 17/06* (2006.01)
(Continued)

(52) U.S. Cl.
CPC ....... *A61M 1/916* (2021.05); *A61B 17/06166* (2013.01); *A61F 13/00051* (2013.01);
(Continued)

(58) Field of Classification Search
CPC .......... A61M 35/00; A61M 1/00; A61M 3/00; A61M 31/00; A61M 1/916; A61M 1/73;
(Continued)

(56) References Cited

U.S. PATENT DOCUMENTS

| 695,270 A | 3/1902 | Beringer |
| 3,014,483 A | 12/1961 | Frank et al. |
(Continued)

FOREIGN PATENT DOCUMENTS

| AU | 2012261793 B2 | 11/2014 |
| AU | 2013206230 B2 | 5/2016 |
(Continued)

OTHER PUBLICATIONS

Cinterion., "Cinterion PHS8-P 3G HSPA+," retrieved from http://www.cinterion.com/tl_files/cinterion/downloads/cinterion_datasheet_PHSS_web.pdf, 2012, 2 pages.
(Continued)

*Primary Examiner* — Susan S Su
*Assistant Examiner* — Eric Rassavong
(74) *Attorney, Agent, or Firm* — Knobbe, Martens, Olson & Bear, LLP

(57) ABSTRACT

Some arrangements disclosed herein relate to devices and methods for treating a wound, comprising applying negative pressure to the wound through a cover applied over a wound, monitoring the internal pressure in the wound, and controlling the closure of the wound by controlling the amount that a wound packing material positioned under the cover collapses within the wound based on the monitored internal pressure. The wound packing material collapse can be controlled to ensure that the monitored internal pressure does not exceed a threshold value. Additionally, some embodiments or arrangements disclosed herein relate to a visualization element to visualize a location of a wound surface. The visualization element can comprise a radiopaque member that is configured to be positioned on or adjacent to a surface of an open wound.

8 Claims, 20 Drawing Sheets

Related U.S. Application Data continuation of application No. 14/402,976, filed as application No. PCT/IB2013/001562 on May 21, 2013, now Pat. No. 10,070,994.

(60) Provisional application No. 61/782,026, filed on Mar. 14, 2013, provisional application No. 61/681,037, filed on Aug. 8, 2012, provisional application No. 61/663,405, filed on Jun. 22, 2012, provisional application No. 61/650,391, filed on May 22, 2012.

(51) Int. Cl.
| | |
|---|---|
| *A61F 13/00* | (2024.01) |
| *A61F 13/01* | (2024.01) |
| *A61F 13/05* | (2024.01) |
| *A61F 13/14* | (2006.01) |
| *A61F 13/44* | (2006.01) |
| *A61B 90/00* | (2016.01) |

(52) U.S. Cl.
CPC .. *A61F 13/00055* (2013.01); *A61F 13/01029* (2024.01); *A61F 13/01034* (2024.01); *A61F 13/05* (2024.01); *A61F 13/148* (2013.01); *A61F 13/44* (2013.01); *A61M 1/73* (2021.05); *A61M 1/732* (2021.05); *A61M 1/915* (2021.05); *A61M 1/966* (2021.05); *A61B 2017/06176* (2013.01); *A61B 2090/3966* (2016.02); *A61F 2013/00174* (2013.01); *A61F 2013/00357* (2013.01); *A61F 2013/00412* (2013.01); *A61F 2013/00536* (2013.01); *A61F 2013/0054* (2013.01); *A61M 2205/3344* (2013.01)

(58) Field of Classification Search
CPC ...... A61M 1/732; A61M 1/915; A61M 1/966; A61M 2205/3344; A61M 2210/1021; A61F 13/00; A61F 13/02; A61F 8/44; A61F 13/00029; A61F 13/00034; A61F 13/00051; A61F 13/00055; A61F 13/00068; A61F 13/148; A61F 13/44; A61F 2013/00174; A61F 2013/00357; A61F 2013/00412; A61F 2013/00536; A61F 2013/0054; A61F 13/01029; A61F 13/01034; A61F 13/05; A61B 17/06166; A61B 2017/06176; A61B 2090/3966
See application file for complete search history.

(56) References Cited

U.S. PATENT DOCUMENTS

| | | | |
|---|---|---|---|
| 3,194,239 | A | 7/1965 | Sullivan et al. |
| 3,578,003 | A | 5/1971 | Everett |
| 3,789,851 | A | 2/1974 | LeVeen |
| 3,812,616 | A | 5/1974 | Koziol |
| 4,467,805 | A | 8/1984 | Fukuda |
| 4,608,041 | A | 8/1986 | Nielsen |
| 4,637,819 | A | 1/1987 | Ouellette et al. |
| 4,699,134 | A | 10/1987 | Samuelsen |
| 4,815,468 | A | 3/1989 | Annand |
| 4,832,299 | A | 5/1989 | Gorton et al. |
| 5,176,663 | A | 1/1993 | Svedman et al. |
| 5,219,428 | A | 6/1993 | Stern |
| 5,264,218 | A | 11/1993 | Rogozinski |
| 5,368,910 | A | 11/1994 | Langdon |
| 5,376,067 | A | 12/1994 | Daneshvar |
| 5,409,472 | A | 4/1995 | Rawlings et al. |
| 5,415,715 | A | 5/1995 | Delage et al. |
| 5,423,857 | A | 6/1995 | Rosenman et al. |
| 5,466,229 | A | 11/1995 | Elson et al. |
| 5,473,536 | A | 12/1995 | Wimmer |
| 5,512,041 | A | 4/1996 | Bogart |
| 5,514,105 | A | 5/1996 | Goodman, Jr. et al. |
| 5,562,107 | A | 10/1996 | Lavender et al. |
| 5,582,601 | A | 12/1996 | Wortrich et al. |
| 5,584,824 | A | 12/1996 | Gillette et al. |
| 5,584,859 | A | 12/1996 | Brotz |
| 5,636,643 | A | 6/1997 | Argenta et al. |
| 5,656,027 | A | 8/1997 | Ellingboe |
| 5,669,892 | A | 9/1997 | Keogh et al. |
| 5,693,013 | A | 12/1997 | Geuder |
| 5,695,777 | A | 12/1997 | Donovan et al. |
| 5,928,210 | A | 7/1999 | Ouellette et al. |
| 5,960,403 | A | 9/1999 | Brown |
| 5,960,497 | A | 10/1999 | Castellino et al. |
| 6,055,506 | A | 4/2000 | Frasca et al. |
| 6,080,168 | A | 6/2000 | Levin et al. |
| 6,086,591 | A | 7/2000 | Bojarski |
| 6,142,982 | A | 11/2000 | Hunt et al. |
| 6,176,868 | B1 | 1/2001 | Detour |
| 6,291,050 | B1 | 9/2001 | Cree et al. |
| 6,336,900 | B1 | 1/2002 | Alleckson et al. |
| 6,353,445 | B1 | 3/2002 | Babula et al. |
| 6,375,614 | B1 | 4/2002 | Braun et al. |
| 6,385,622 | B2 | 5/2002 | Bouve et al. |
| 6,406,426 | B1 | 6/2002 | Reuss et al. |
| 6,434,572 | B2 | 8/2002 | Derzay et al. |
| 6,460,041 | B2 | 10/2002 | Lloyd |
| 6,503,208 | B1 | 1/2003 | Skovlund |
| 6,530,941 | B1 | 3/2003 | Muller et al. |
| 6,548,727 | B1 | 4/2003 | Swenson |
| 6,553,998 | B2 | 4/2003 | Heaton et al. |
| 6,566,575 | B1 | 5/2003 | Stickels et al. |
| 6,574,518 | B1 | 6/2003 | Lounsberry et al. |
| 6,640,145 | B2 | 10/2003 | Hoffberg et al. |
| 6,640,246 | B1 | 10/2003 | Gary et al. |
| 6,675,131 | B2 | 1/2004 | Hahn |
| 6,681,003 | B2 | 1/2004 | Linder et al. |
| 6,685,681 | B2 | 2/2004 | Lockwood et al. |
| 6,695,823 | B1 | 2/2004 | Lina et al. |
| 6,712,830 | B2 | 3/2004 | Esplin |
| 6,712,839 | B1 | 3/2004 | Lonne |
| 6,723,046 | B2 | 4/2004 | Lichtenstein et al. |
| 6,730,024 | B2 | 5/2004 | Freyre et al. |
| 6,747,556 | B2 | 6/2004 | Medema et al. |
| 6,755,807 | B2 | 6/2004 | Risk, Jr. et al. |
| 6,767,334 | B1 | 7/2004 | Randolph |
| 6,770,794 | B2 | 8/2004 | Fleischmann |
| 6,776,769 | B2 | 8/2004 | Smith |
| 6,779,024 | B2 | 8/2004 | DeLaHuerga |
| 6,782,285 | B2 | 8/2004 | Birkenbach et al. |
| 6,787,682 | B2 | 9/2004 | Gilman |
| 6,855,135 | B2 | 2/2005 | Lockwood et al. |
| 6,856,825 | B2 | 2/2005 | Hahn |
| 6,868,528 | B2 | 3/2005 | Roberts |
| 6,871,211 | B2 | 3/2005 | Labounty et al. |
| 6,883,531 | B1 | 4/2005 | Perttu |
| 6,893,452 | B2 | 5/2005 | Jacobs |
| 6,909,974 | B2 | 6/2005 | Yung et al. |
| 6,912,481 | B2 | 6/2005 | Breunissen et al. |
| 6,936,037 | B2 | 8/2005 | Bubb et al. |
| 6,951,553 | B2 | 10/2005 | Bubb et al. |
| 6,961,731 | B2 | 11/2005 | Holbrook |
| 6,977,323 | B1 | 12/2005 | Swenson |
| 6,979,324 | B2 | 12/2005 | Bybordi et al. |
| 6,994,702 | B1 | 2/2006 | Johnson |
| 7,004,915 | B2 | 2/2006 | Boynton et al. |
| 7,022,113 | B2 | 4/2006 | Lockwood et al. |
| 7,025,755 | B2 | 4/2006 | Epstein et al. |
| 7,051,012 | B2 | 5/2006 | Cole et al. |
| 7,062,251 | B2 | 6/2006 | Birkett et al. |
| 7,066,883 | B2 | 6/2006 | Schmidt et al. |
| 7,070,584 | B2 | 7/2006 | Johnson et al. |
| 7,103,578 | B2 | 9/2006 | Beck et al. |
| 7,108,683 | B2 | 9/2006 | Zamierowski |
| 7,120,488 | B2 | 10/2006 | Nova et al. |
| 7,128,735 | B2 | 10/2006 | Weston |
| 7,133,869 | B2 | 11/2006 | Bryan et al. |
| 7,144,390 | B1 | 12/2006 | Hannigan et al. |
| 7,153,312 | B1 | 12/2006 | Torrie et al. |

(56) References Cited

U.S. PATENT DOCUMENTS

| | | |
|---|---|---|
| 7,156,862 B2 | 1/2007 | Jacobs et al. |
| 7,167,858 B2 | 1/2007 | Naeymi-Rad et al. |
| 7,172,615 B2 | 2/2007 | Morriss et al. |
| 7,189,238 B2 | 3/2007 | Lombardo et al. |
| 7,196,054 B1 | 3/2007 | Drohan et al. |
| 7,212,829 B1 | 5/2007 | Lau et al. |
| D544,092 S | 6/2007 | Lewis |
| 7,262,174 B2 | 8/2007 | Jiang et al. |
| 7,264,591 B2 | 9/2007 | Brown |
| 7,279,612 B1 | 10/2007 | Heaton et al. |
| 7,300,418 B2 | 11/2007 | Zaleski |
| 7,304,573 B2 | 12/2007 | Postma |
| 7,311,665 B2 | 12/2007 | Hawthorne et al. |
| 7,315,183 B2 | 1/2008 | Hinterscher |
| 7,333,002 B2 | 2/2008 | Bixler et al. |
| 7,351,250 B2 | 4/2008 | Zamierowski |
| 7,353,179 B2 | 4/2008 | Ott et al. |
| 7,361,184 B2 | 4/2008 | Joshi |
| 7,367,342 B2 | 5/2008 | Butler |
| 7,381,211 B2 | 6/2008 | Zamierowski |
| 7,381,859 B2 | 6/2008 | Hunt et al. |
| 7,384,267 B1 | 6/2008 | Franks et al. |
| 7,413,571 B2 | 8/2008 | Zamierowski |
| 7,430,598 B2 | 9/2008 | Raden et al. |
| 7,430,608 B2 | 9/2008 | Noonan et al. |
| 7,438,705 B2 | 10/2008 | Karpowicz et al. |
| 7,451,002 B2 | 11/2008 | Choubey |
| 7,457,804 B2 | 11/2008 | Uber et al. |
| 7,460,872 B2 | 12/2008 | Millard et al. |
| 7,494,482 B2 | 2/2009 | Orgill et al. |
| 7,534,240 B1 | 5/2009 | Johnson |
| 7,553,306 B1 | 6/2009 | Hunt et al. |
| 7,553,923 B2 | 6/2009 | Williams et al. |
| 7,569,742 B2 | 8/2009 | Haggstrom et al. |
| 7,578,532 B2 | 8/2009 | Schiebler |
| D602,583 S | 10/2009 | Pidgeon et al. |
| 7,598,855 B2 | 10/2009 | Scalisi et al. |
| 7,608,066 B2 | 10/2009 | Vogel |
| 7,611,500 B1 | 11/2009 | Lina et al. |
| 7,612,248 B2 | 11/2009 | Burton et al. |
| 7,615,036 B2 | 11/2009 | Joshi et al. |
| 7,617,762 B1 | 11/2009 | Ragner |
| 7,618,382 B2 | 11/2009 | Vogel et al. |
| 7,622,629 B2 | 11/2009 | Aali |
| 7,625,362 B2 | 12/2009 | Boehringer et al. |
| 7,627,334 B2 | 12/2009 | Cohen et al. |
| 7,645,269 B2 | 1/2010 | Zamierowski |
| 7,649,449 B2 | 1/2010 | Fenske et al. |
| 7,651,484 B2 | 1/2010 | Heaton et al. |
| 7,671,733 B2 | 3/2010 | McNeal et al. |
| 7,678,102 B1 | 3/2010 | Heaton |
| 7,683,667 B2 | 3/2010 | Kim |
| 7,684,999 B2 | 3/2010 | Brown |
| 7,698,156 B2 | 4/2010 | Martucci et al. |
| 7,699,823 B2 | 4/2010 | Haggstrom et al. |
| 7,699,830 B2 | 4/2010 | Martin |
| 7,699,831 B2 | 4/2010 | Bengtson et al. |
| 7,700,819 B2 | 4/2010 | Ambrosio et al. |
| 7,708,724 B2 | 5/2010 | Weston |
| 7,713,743 B2 | 5/2010 | Villanueva et al. |
| 7,722,528 B2 | 5/2010 | Arnal et al. |
| 7,723,560 B2 | 5/2010 | Lockwood et al. |
| 7,734,764 B2 | 6/2010 | Weiner et al. |
| 7,749,164 B2 | 7/2010 | Davis |
| 7,754,937 B2 | 7/2010 | Boehringer et al. |
| 7,776,028 B2 | 8/2010 | Miller et al. |
| 7,777,522 B2 | 8/2010 | Yang et al. |
| 7,779,153 B2 | 8/2010 | Van den Heuvel et al. |
| 7,779,625 B2 | 8/2010 | Joshi et al. |
| 7,789,828 B2 | 9/2010 | Clapp |
| 7,794,438 B2 | 9/2010 | Henley et al. |
| 7,815,616 B2 | 10/2010 | Boehringer et al. |
| 7,820,453 B2 | 10/2010 | Heylen et al. |
| 7,827,148 B2 | 11/2010 | Mori et al. |
| 7,846,141 B2 | 12/2010 | Weston |
| 7,857,806 B2 | 12/2010 | Karpowicz et al. |
| 7,858,835 B2 | 12/2010 | Abuzaina et al. |
| 7,862,339 B2 | 1/2011 | Mulligan |
| 7,863,495 B2 | 1/2011 | Aali |
| 7,865,375 B2 | 1/2011 | Lancaster et al. |
| 7,889,069 B2 | 2/2011 | Fifolt et al. |
| 7,890,887 B1 | 2/2011 | Linardos et al. |
| 7,892,181 B2 | 2/2011 | Christensen et al. |
| 7,896,856 B2 | 3/2011 | Petrosenko et al. |
| 7,909,805 B2 | 3/2011 | Weston |
| 7,910,789 B2 | 3/2011 | Sinyagin |
| 7,912,823 B2 | 3/2011 | Ferrari et al. |
| 7,925,603 B1 | 4/2011 | Laidig et al. |
| 7,931,774 B2 | 4/2011 | Hall et al. |
| 7,933,817 B2 | 4/2011 | Radl et al. |
| 7,942,866 B2 | 5/2011 | Radl et al. |
| 7,964,766 B2 | 6/2011 | Blott et al. |
| 7,976,519 B2 | 7/2011 | Bubb et al. |
| 7,976,524 B2 | 7/2011 | Kudo et al. |
| 7,988,850 B2 | 8/2011 | Roncadi et al. |
| 8,015,443 B2 | 9/2011 | Adachi |
| 8,015,972 B2 | 9/2011 | Pirzada |
| 8,019,618 B2 | 9/2011 | Brown |
| 8,030,534 B2 | 10/2011 | Radl et al. |
| 8,036,925 B2 | 10/2011 | Choubey |
| 8,048,046 B2 | 11/2011 | Hudspeth et al. |
| 8,054,950 B1 | 11/2011 | Hung et al. |
| 8,057,447 B2 | 11/2011 | Olson et al. |
| 8,061,360 B2 | 11/2011 | Locke et al. |
| 8,062,272 B2 | 11/2011 | Weston |
| 8,062,295 B2 | 11/2011 | McDevitt et al. |
| 8,062,331 B2 | 11/2011 | Zamierowski |
| 8,067,662 B2 | 11/2011 | Aali et al. |
| 8,069,057 B2 | 11/2011 | Choubey et al. |
| 8,094,009 B2 | 1/2012 | Allen et al. |
| 8,100,887 B2 | 1/2012 | Weston et al. |
| 8,105,295 B2 | 1/2012 | Blott |
| 8,114,126 B2 | 2/2012 | Heaton et al. |
| 8,123,781 B2 | 2/2012 | Zamierowski |
| 8,126,735 B2 | 2/2012 | Dicks et al. |
| 8,129,580 B2 | 3/2012 | Wilkes et al. |
| 8,130,095 B2 | 3/2012 | Allen et al. |
| 8,131,472 B2 | 3/2012 | Chow et al. |
| 8,142,419 B2 | 3/2012 | Heaton et al. |
| 8,162,909 B2 | 4/2012 | Blott et al. |
| 8,167,869 B2 | 5/2012 | Wudyka |
| 8,172,816 B2 | 5/2012 | Kazala, Jr. et al. |
| 8,180,750 B2 | 5/2012 | Wilmering et al. |
| 8,182,413 B2 | 5/2012 | Browning |
| 8,187,237 B2 | 5/2012 | Seegert |
| 8,188,331 B2 | 5/2012 | Barta et al. |
| 8,190,445 B2 | 5/2012 | Kuth et al. |
| 8,190,448 B2 | 5/2012 | Bajars et al. |
| 8,192,409 B2 | 6/2012 | Hardman et al. |
| 8,197,467 B2 | 6/2012 | Heaton et al. |
| 8,228,188 B2 | 7/2012 | Key et al. |
| 8,235,955 B2 | 8/2012 | Blott et al. |
| 8,235,972 B2 | 8/2012 | Adahan |
| 8,246,606 B2 | 8/2012 | Stevenson et al. |
| 8,249,894 B2 | 8/2012 | Brown |
| 8,255,241 B2 | 8/2012 | Cafer |
| 8,257,328 B2 | 9/2012 | Augustine et al. |
| 8,260,630 B2 | 9/2012 | Brown |
| 8,267,918 B2 | 9/2012 | Johnson et al. |
| 8,273,105 B2 | 9/2012 | Cohen et al. |
| 8,280,682 B2 | 10/2012 | Vock et al. |
| 8,284,046 B2 | 10/2012 | Allen et al. |
| 8,290,792 B2 | 10/2012 | Sekura |
| 8,291,337 B2 | 10/2012 | Gannin et al. |
| 8,294,586 B2 | 10/2012 | Pidgeon et al. |
| 8,308,714 B2 | 11/2012 | Weston et al. |
| 8,323,263 B2 | 12/2012 | Wood et al. |
| 8,328,776 B2 | 12/2012 | Kelch et al. |
| 8,332,233 B2 | 12/2012 | Ott et al. |
| 8,332,236 B2 | 12/2012 | Yurko et al. |
| 8,334,768 B2 | 12/2012 | Eaton et al. |
| 8,337,411 B2 | 12/2012 | Nishtala et al. |
| 8,337,482 B2 | 12/2012 | Wood et al. |
| 8,353,931 B2 | 1/2013 | Stopek et al. |

(56) References Cited

U.S. PATENT DOCUMENTS

| | | |
|---|---|---|
| 8,357,131 B2 | 1/2013 | Olson |
| 8,360,975 B1 | 1/2013 | Schwieterman et al. |
| 8,366,690 B2 | 2/2013 | Locke et al. |
| 8,366,692 B2 | 2/2013 | Weston et al. |
| 8,376,972 B2 | 2/2013 | Fleischmann |
| 8,399,730 B2 | 3/2013 | Kazala, Jr. et al. |
| 8,400,295 B1 | 3/2013 | Khaira |
| 8,409,170 B2 | 4/2013 | Locke et al. |
| 8,422,377 B2 | 4/2013 | Weiner et al. |
| 8,424,517 B2 | 4/2013 | Sutherland et al. |
| 8,430,867 B2 | 4/2013 | Robinson et al. |
| 8,436,871 B2 | 5/2013 | Alberte |
| 8,439,882 B2 | 5/2013 | Kelch |
| 8,444,392 B2 | 5/2013 | Turner et al. |
| 8,447,375 B2 | 5/2013 | Shuler |
| 8,449,508 B2 | 5/2013 | Coulthard et al. |
| 8,454,990 B2 | 6/2013 | Canada et al. |
| 8,457,740 B2 | 6/2013 | Osche |
| 8,460,257 B2 | 6/2013 | Locke et al. |
| 8,480,641 B2 | 7/2013 | Jacobs |
| 8,481,804 B2 | 7/2013 | Timothy |
| 8,486,032 B2 | 7/2013 | Seegert et al. |
| 8,494,349 B2 | 7/2013 | Gordon |
| 8,500,776 B2 | 8/2013 | Ebner |
| 8,515,776 B2 | 8/2013 | Schoenberg |
| 8,532,764 B2 | 9/2013 | Duke |
| 8,535,296 B2 | 9/2013 | Blott et al. |
| 8,540,688 B2 | 9/2013 | Eckstein et al. |
| 8,545,483 B2 | 10/2013 | Schwabe et al. |
| 8,554,195 B2 | 10/2013 | Rao |
| 8,554,902 B2 | 10/2013 | Ebert et al. |
| 8,558,964 B2 | 10/2013 | Bedingfield |
| 8,560,082 B2 | 10/2013 | Wei |
| 8,577,694 B2 | 11/2013 | Kanaan |
| 8,595,553 B2 | 11/2013 | Goertler et al. |
| 8,600,777 B2 | 12/2013 | Schoenberg et al. |
| 8,608,776 B2 | 12/2013 | Coward et al. |
| 8,622,981 B2 | 1/2014 | Hartwell et al. |
| 8,626,342 B2 | 1/2014 | Williams et al. |
| 8,626,526 B2 | 1/2014 | Lemke et al. |
| 8,630,660 B2 | 1/2014 | Ray et al. |
| 8,632,485 B2 | 1/2014 | Schlaeper et al. |
| 8,632,523 B2 | 1/2014 | Eriksson et al. |
| 8,641,693 B2 | 2/2014 | Locke et al. |
| 8,657,806 B2 | 2/2014 | Eckstein et al. |
| 8,659,420 B2 | 2/2014 | Salvat et al. |
| 8,668,677 B2 | 3/2014 | Eckstein et al. |
| 8,673,992 B2 | 3/2014 | Eckstein et al. |
| 8,676,597 B2 | 3/2014 | Buehler et al. |
| 8,679,080 B2 | 3/2014 | Kazala, Jr. et al. |
| 8,679,153 B2 | 3/2014 | Dennis |
| 8,680,360 B2 | 3/2014 | Greener et al. |
| 8,689,008 B2 | 4/2014 | Rangadass et al. |
| 8,694,600 B2 | 4/2014 | Gaines et al. |
| 8,706,537 B1 | 4/2014 | Young et al. |
| 8,721,629 B2 | 5/2014 | Hardman et al. |
| 8,725,528 B2 | 5/2014 | Locke et al. |
| 8,746,662 B2 | 6/2014 | Poppe |
| 8,747,375 B2 | 6/2014 | Barta et al. |
| 8,756,078 B2 | 6/2014 | Collins et al. |
| 8,757,485 B2 | 6/2014 | Drees et al. |
| 8,758,315 B2 | 6/2014 | Chen et al. |
| 8,764,732 B2 | 7/2014 | Hartwell |
| 8,768,441 B2 | 7/2014 | De Zwart et al. |
| 8,769,625 B2 | 7/2014 | Wang et al. |
| 8,771,259 B2 | 7/2014 | Karpowicz et al. |
| 8,781,847 B2 | 7/2014 | Simms et al. |
| 8,784,392 B2 | 7/2014 | Vess et al. |
| 8,791,315 B2 | 7/2014 | Lattimore et al. |
| 8,791,316 B2 | 7/2014 | Greener |
| 8,795,171 B2 | 8/2014 | Adamczyk |
| 8,795,244 B2 | 8/2014 | Randolph et al. |
| 8,802,916 B2 | 8/2014 | Griffey et al. |
| 8,814,840 B2 | 8/2014 | Evans et al. |
| 8,814,841 B2 | 8/2014 | Hartwell |
| 8,821,535 B2 | 9/2014 | Greener |
| 8,827,983 B2 | 9/2014 | Braga et al. |
| 8,838,136 B2 | 9/2014 | Carnes et al. |
| 8,843,327 B2 | 9/2014 | Vernon-Harcourt et al. |
| 8,845,603 B2 | 9/2014 | Middleton et al. |
| 8,858,517 B2 | 10/2014 | Pan et al. |
| 8,862,393 B2 | 10/2014 | Zhou et al. |
| 8,868,794 B2 | 10/2014 | Masoud et al. |
| 8,874,035 B2 | 10/2014 | Sherman et al. |
| 8,882,730 B2 | 11/2014 | Zimnitsky et al. |
| 8,887,100 B1 | 11/2014 | Cook et al. |
| 8,890,656 B2 | 11/2014 | Pendse |
| 8,897,198 B2 | 11/2014 | Gaines et al. |
| 8,902,278 B2 | 12/2014 | Pinter et al. |
| 8,905,959 B2 | 12/2014 | Basaglia |
| 8,909,595 B2 | 12/2014 | Gandy et al. |
| 8,912,897 B2 | 12/2014 | Carnes |
| 8,922,377 B2 | 12/2014 | Carnes |
| 8,945,073 B2 | 2/2015 | Croizat et al. |
| 8,947,237 B2 | 2/2015 | Margon et al. |
| 8,976,062 B2 | 3/2015 | Park et al. |
| 8,978,026 B2 | 3/2015 | Charlton et al. |
| 8,996,393 B2 | 3/2015 | Sobie |
| 9,044,579 B2 | 6/2015 | Blott et al. |
| 9,047,648 B1 | 6/2015 | Lekutai et al. |
| 9,050,398 B2 | 6/2015 | Armstrong et al. |
| 9,058,634 B2 | 6/2015 | Buan et al. |
| 9,081,885 B2 | 7/2015 | Bangera et al. |
| 9,087,141 B2 | 7/2015 | Huang et al. |
| 9,092,705 B2 | 7/2015 | Zhuang |
| 9,098,114 B2 | 8/2015 | Potter et al. |
| 9,105,006 B2 | 8/2015 | Williamson |
| 9,114,054 B2 | 8/2015 | Bennett |
| 9,117,012 B2 | 8/2015 | Basaglia |
| 9,135,398 B2 | 9/2015 | Kaib et al. |
| 9,141,270 B1 | 9/2015 | Stuart et al. |
| 9,159,148 B2 | 10/2015 | Boyer et al. |
| 9,180,231 B2 | 11/2015 | Greener |
| 9,204,801 B2 | 12/2015 | Locke et al. |
| 9,215,516 B2 | 12/2015 | Carnes et al. |
| 9,215,581 B2 | 12/2015 | Julian et al. |
| 9,220,822 B2 | 12/2015 | Hartwell |
| 9,230,420 B2 | 1/2016 | Lee et al. |
| 9,268,827 B2 | 2/2016 | Fernandez |
| 9,286,443 B2 | 3/2016 | Ford et al. |
| 9,323,893 B2 | 4/2016 | Berry et al. |
| 9,332,363 B2 | 5/2016 | Jain et al. |
| 9,339,248 B2 | 5/2016 | Tout et al. |
| 9,393,354 B2 | 7/2016 | Freedman et al. |
| 9,408,755 B2 | 8/2016 | Larsson |
| 9,436,645 B2 | 9/2016 | Al-Ali et al. |
| 9,436,800 B2 | 9/2016 | Forrester |
| 9,460,431 B2 | 10/2016 | Curry |
| 9,545,466 B2 | 1/2017 | Locke et al. |
| 9,558,331 B2 | 1/2017 | Orona et al. |
| 9,585,565 B2 | 3/2017 | Carnes |
| 9,589,247 B2 | 3/2017 | Bolene et al. |
| 9,602,952 B2 | 3/2017 | Kang et al. |
| 9,629,986 B2 | 4/2017 | Patel et al. |
| 9,658,066 B2 | 5/2017 | Yuen et al. |
| 9,662,438 B2 | 5/2017 | Kamen et al. |
| 9,687,618 B2 | 6/2017 | Steinhauer et al. |
| 9,693,691 B2 | 7/2017 | Johnson |
| 9,737,649 B2 | 8/2017 | Begin et al. |
| 9,741,084 B2 | 8/2017 | Holmes et al. |
| 9,757,500 B2 | 9/2017 | Locke et al. |
| 9,792,660 B2 | 10/2017 | Cannon et al. |
| 9,818,164 B2 | 11/2017 | Nolte et al. |
| 9,849,023 B2 | 12/2017 | Hall et al. |
| 9,878,081 B2 | 1/2018 | Leiendecker et al. |
| 9,905,123 B2 | 2/2018 | Lawhorn |
| 9,928,478 B2 | 3/2018 | Ragusky et al. |
| 9,990,466 B2 | 6/2018 | DeBusk et al. |
| 9,996,681 B2 | 6/2018 | Suarez et al. |
| 10,049,346 B2 | 8/2018 | Jensen et al. |
| 10,061,894 B2 | 8/2018 | Sethumadhavan et al. |
| 10,070,994 B2 | 9/2018 | Dodd et al. |
| 10,117,782 B2 | 11/2018 | Dagger et al. |
| 10,124,098 B2 | 11/2018 | Dunn et al. |

(56) References Cited

U.S. PATENT DOCUMENTS

| | | | |
|---|---|---|---|
| 10,173,008 B2 | 1/2019 | Simpson et al. |
| 10,185,834 B2 | 1/2019 | Adam et al. |
| 10,207,031 B2 | 2/2019 | Toth |
| 10,328,188 B2 | 6/2019 | Deutsch et al. |
| 10,537,657 B2 | 1/2020 | Phillips et al. |
| 11,123,226 B2 * | 9/2021 | Dodd | A61F 13/00068 |
| 2001/0034499 A1 | 10/2001 | Sessions et al. |
| 2002/0022861 A1 | 2/2002 | Jacobs et al. |
| 2002/0026160 A1 | 2/2002 | Takahashi et al. |
| 2002/0077661 A1 | 6/2002 | Saadat |
| 2002/0087360 A1 | 7/2002 | Pettit |
| 2002/0128804 A1 | 9/2002 | Geva |
| 2002/0128869 A1 | 9/2002 | Kuth |
| 2002/0135336 A1 | 9/2002 | Zhou et al. |
| 2002/0177757 A1 | 11/2002 | Britton |
| 2002/0184055 A1 | 12/2002 | Naghavi et al. |
| 2003/0009244 A1 | 1/2003 | Engleson et al. |
| 2003/0018736 A1 | 1/2003 | Christ et al. |
| 2003/0093041 A1 | 5/2003 | Risk, Jr. et al. |
| 2003/0105649 A1 | 6/2003 | Sheiner et al. |
| 2003/0114816 A1 | 6/2003 | Underhill et al. |
| 2003/0114818 A1 | 6/2003 | Benecke et al. |
| 2003/0114821 A1 | 6/2003 | Underhill et al. |
| 2003/0120249 A1 | 6/2003 | Wulz et al. |
| 2003/0121588 A1 | 7/2003 | Pargass et al. |
| 2003/0164600 A1 | 9/2003 | Dunn et al. |
| 2003/0182158 A1 | 9/2003 | Son |
| 2003/0220660 A1 | 11/2003 | Kortenbach et al. |
| 2003/0221687 A1 | 12/2003 | Kaigler |
| 2003/0229518 A1 | 12/2003 | Abraham-Fuchs et al. |
| 2004/0006492 A1 | 1/2004 | Watanabe |
| 2004/0010275 A1 | 1/2004 | Jacobs et al. |
| 2004/0054346 A1 | 3/2004 | Zhu et al. |
| 2004/0054775 A1 | 3/2004 | Poliac et al. |
| 2004/0078223 A1 | 4/2004 | Sacco et al. |
| 2004/0102743 A1 | 5/2004 | Walker |
| 2004/0143458 A1 | 7/2004 | Pulkkinen et al. |
| 2004/0162512 A1 | 8/2004 | Liedtke et al. |
| 2004/0167802 A1 | 8/2004 | Takada et al. |
| 2004/0167804 A1 | 8/2004 | Simpson et al. |
| 2004/0172301 A1 | 9/2004 | Mihai et al. |
| 2004/0181433 A1 | 9/2004 | Blair |
| 2004/0193449 A1 | 9/2004 | Wildman et al. |
| 2004/0204962 A1 | 10/2004 | Howser et al. |
| 2004/0267312 A1 | 12/2004 | Kanner et al. |
| 2005/0033124 A1 | 2/2005 | Kelly et al. |
| 2005/0055225 A1 | 3/2005 | Mehl |
| 2005/0055242 A1 | 3/2005 | Bello et al. |
| 2005/0055244 A1 | 3/2005 | Mullan et al. |
| 2005/0060211 A1 | 3/2005 | Xiao et al. |
| 2005/0065817 A1 | 3/2005 | Mihai et al. |
| 2005/0097200 A1 | 5/2005 | Denning, Jr. et al. |
| 2005/0102167 A1 | 5/2005 | Kapoor |
| 2005/0107731 A1 | 5/2005 | Sessions |
| 2005/0108046 A1 | 5/2005 | Craft |
| 2005/0108057 A1 | 5/2005 | Cohen et al. |
| 2005/0114176 A1 | 5/2005 | Dominick et al. |
| 2005/0119694 A1 | 6/2005 | Jacobs et al. |
| 2005/0119914 A1 | 6/2005 | Batch |
| 2005/0124966 A1 | 6/2005 | Karpowicz et al. |
| 2005/0142331 A1 | 6/2005 | Anderson et al. |
| 2005/0187528 A1 | 8/2005 | Berg |
| 2005/0209560 A1 | 9/2005 | Boukhny et al. |
| 2005/0222613 A1 | 10/2005 | Ryan |
| 2005/0222873 A1 | 10/2005 | Nephin et al. |
| 2005/0240111 A1 | 10/2005 | Chung |
| 2005/0258887 A1 | 11/2005 | Ito et al. |
| 2005/0267424 A1 | 12/2005 | Eriksson et al. |
| 2005/0283382 A1 | 12/2005 | Donoghue et al. |
| 2006/0004604 A1 | 1/2006 | White |
| 2006/0020269 A1 | 1/2006 | Cheng |
| 2006/0029675 A1 | 2/2006 | Ginther |
| 2006/0058842 A1 | 3/2006 | Wilke et al. |
| 2006/0064124 A1 | 3/2006 | Zhu et al. |
| 2006/0064323 A1 | 3/2006 | Alleckson et al. |
| 2006/0069357 A1 | 3/2006 | Marasco |
| 2006/0079599 A1 | 4/2006 | Arthur |
| 2006/0085393 A1 | 4/2006 | Modesitt |
| 2006/0089539 A1 | 4/2006 | Miodownik et al. |
| 2006/0095853 A1 | 5/2006 | Amyot et al. |
| 2006/0135921 A1 | 6/2006 | Wiercinski et al. |
| 2006/0144440 A1 | 7/2006 | Merkle |
| 2006/0155584 A1 | 7/2006 | Aggarwal |
| 2006/0161460 A1 | 7/2006 | Smitherman et al. |
| 2006/0190130 A1 | 8/2006 | Fedor et al. |
| 2006/0195843 A1 | 8/2006 | Hall |
| 2006/0217795 A1 | 9/2006 | Besselink et al. |
| 2006/0224051 A1 | 10/2006 | Teller et al. |
| 2006/0246922 A1 | 11/2006 | Gasbarro et al. |
| 2006/0257457 A1 | 11/2006 | Gorman et al. |
| 2006/0259074 A1 | 11/2006 | Kelleher et al. |
| 2006/0271018 A1 | 11/2006 | Korf |
| 2007/0032741 A1 | 2/2007 | Hibner et al. |
| 2007/0032755 A1 | 2/2007 | Walsh |
| 2007/0052144 A1 | 3/2007 | Knirck et al. |
| 2007/0078444 A1 | 4/2007 | Larsson |
| 2007/0104941 A1 | 5/2007 | Kameda et al. |
| 2007/0118096 A1 | 5/2007 | Smith et al. |
| 2007/0123816 A1 | 5/2007 | Zhu et al. |
| 2007/0123973 A1 | 5/2007 | Roth et al. |
| 2007/0129660 A1 | 6/2007 | McLeod et al. |
| 2007/0136099 A1 | 6/2007 | Neligh et al. |
| 2007/0149910 A1 | 6/2007 | Zocher |
| 2007/0156456 A1 | 7/2007 | McGillin et al. |
| 2007/0179421 A1 | 8/2007 | Farrow |
| 2007/0180904 A1 | 8/2007 | Gao |
| 2007/0185463 A1 | 8/2007 | Mulligan |
| 2007/0197881 A1 | 8/2007 | Wolf et al. |
| 2007/0213597 A1 | 9/2007 | Wooster |
| 2007/0219826 A1 | 9/2007 | Brodsky et al. |
| 2007/0255116 A1 | 11/2007 | Mehta et al. |
| 2007/0260226 A1 | 11/2007 | Jaeb et al. |
| 2007/0271298 A1 | 11/2007 | Juang et al. |
| 2007/0282309 A1 | 12/2007 | Bengtson et al. |
| 2007/0282374 A1 | 12/2007 | Sogard et al. |
| 2007/0299541 A1 | 12/2007 | Chernomorsky et al. |
| 2008/0009681 A1 | 1/2008 | Al Hussiny |
| 2008/0015526 A1 | 1/2008 | Reiner et al. |
| 2008/0041401 A1 | 2/2008 | Casola et al. |
| 2008/0051708 A1 | 2/2008 | Kumar et al. |
| 2008/0082040 A1 | 4/2008 | Kubler et al. |
| 2008/0082077 A1 | 4/2008 | Williams |
| 2008/0086357 A1 | 4/2008 | Choubey et al. |
| 2008/0091659 A1 | 4/2008 | McFaul |
| 2008/0108977 A1 | 5/2008 | Heaton et al. |
| 2008/0119705 A1 | 5/2008 | Patel et al. |
| 2008/0125697 A1 | 5/2008 | Gao |
| 2008/0125698 A1 | 5/2008 | Gerg et al. |
| 2008/0126126 A1 | 5/2008 | Ballai |
| 2008/0140160 A1 | 6/2008 | Goetz et al. |
| 2008/0167534 A1 | 7/2008 | Young et al. |
| 2008/0177253 A1 | 7/2008 | Boehringer et al. |
| 2008/0177579 A1 | 7/2008 | Dehaan |
| 2008/0221396 A1 | 9/2008 | Garces et al. |
| 2008/0242945 A1 | 10/2008 | Gugliotti et al. |
| 2008/0243096 A1 | 10/2008 | Svedman |
| 2008/0275409 A1 | 11/2008 | Kane et al. |
| 2008/0287973 A1 | 11/2008 | Aster et al. |
| 2008/0306456 A1 | 12/2008 | Riesinger |
| 2008/0312953 A1 | 12/2008 | Claus |
| 2009/0005746 A1 | 1/2009 | Nielsen et al. |
| 2009/0037220 A1 | 2/2009 | Chambers et al. |
| 2009/0043268 A1 | 2/2009 | Eddy et al. |
| 2009/0048492 A1 | 2/2009 | Rantala et al. |
| 2009/0048865 A1 | 2/2009 | Breazeale, Jr. |
| 2009/0069760 A1 | 3/2009 | Finklestein |
| 2009/0069904 A1 | 3/2009 | Picha |
| 2009/0093550 A1 | 4/2009 | Rolfes et al. |
| 2009/0097623 A1 | 4/2009 | Bharadwaj |
| 2009/0099519 A1 | 4/2009 | Kaplan |
| 2009/0099866 A1 | 4/2009 | Newman |
| 2009/0099867 A1 | 4/2009 | Newman |
| 2009/0101219 A1 | 4/2009 | Martini et al. |
| 2009/0105670 A1 | 4/2009 | Bentley et al. |

(56) References Cited

U.S. PATENT DOCUMENTS

| | | |
|---|---|---|
| 2009/0115663 A1 | 5/2009 | Brown et al. |
| 2009/0118591 A1 | 5/2009 | Kim et al. |
| 2009/0125331 A1 | 5/2009 | Pamsgaard et al. |
| 2009/0136909 A1 | 5/2009 | Asukai et al. |
| 2009/0144091 A1 | 6/2009 | Rago |
| 2009/0157429 A1 | 6/2009 | Lee et al. |
| 2009/0163774 A1 | 6/2009 | Thatha et al. |
| 2009/0171166 A1 | 7/2009 | Amundson et al. |
| 2009/0177495 A1 | 7/2009 | Abousy et al. |
| 2009/0187424 A1 | 7/2009 | Grabowski |
| 2009/0204423 A1 | 8/2009 | DeGheest et al. |
| 2009/0204434 A1 | 8/2009 | Breazeale, Jr. |
| 2009/0204435 A1 | 8/2009 | Gale |
| 2009/0205042 A1 | 8/2009 | Zhou et al. |
| 2009/0224889 A1 | 9/2009 | Aggarwal et al. |
| 2009/0227938 A1 | 9/2009 | Fasching et al. |
| 2009/0227969 A1 | 9/2009 | Jaeb et al. |
| 2009/0246238 A1 | 10/2009 | Gorman et al. |
| 2009/0259203 A1 | 10/2009 | Hu et al. |
| 2009/0270833 A1 | 10/2009 | DeBelser et al. |
| 2009/0281822 A1 | 11/2009 | Warner et al. |
| 2009/0281830 A1 | 11/2009 | McNames et al. |
| 2009/0281867 A1 | 11/2009 | Sievenpiper et al. |
| 2009/0299307 A1 | 12/2009 | Barta et al. |
| 2009/0299342 A1 | 12/2009 | Cavanaugh, II et al. |
| 2009/0312685 A1 | 12/2009 | Olsen et al. |
| 2009/0326339 A1 | 12/2009 | Horvitz |
| 2009/0327102 A1 | 12/2009 | Maniar et al. |
| 2010/0001838 A1 | 1/2010 | Miodownik et al. |
| 2010/0017471 A1 | 1/2010 | Brown et al. |
| 2010/0022848 A1 | 1/2010 | Lee et al. |
| 2010/0022990 A1 | 1/2010 | Karpowicz et al. |
| 2010/0028407 A1 | 2/2010 | Del Priore et al. |
| 2010/0030132 A1 | 2/2010 | Niezgoda et al. |
| 2010/0030302 A1 | 2/2010 | Blowers et al. |
| 2010/0036333 A1 | 2/2010 | Schenk, III et al. |
| 2010/0042059 A1 | 2/2010 | Pratt et al. |
| 2010/0047324 A1 | 2/2010 | Fritz et al. |
| 2010/0069863 A1 | 3/2010 | Olson |
| 2010/0081983 A1 | 4/2010 | Zocher et al. |
| 2010/0090004 A1 | 4/2010 | Sands et al. |
| 2010/0106528 A1 | 4/2010 | Brackett et al. |
| 2010/0113908 A1 | 5/2010 | Vargas et al. |
| 2010/0121257 A1 | 5/2010 | King |
| 2010/0126268 A1 | 5/2010 | Baily et al. |
| 2010/0137775 A1 | 6/2010 | Hu et al. |
| 2010/0137890 A1 | 6/2010 | Martinez et al. |
| 2010/0145161 A1 | 6/2010 | Niyato et al. |
| 2010/0150991 A1 | 6/2010 | Bernstein |
| 2010/0160874 A1 | 6/2010 | Robinson et al. |
| 2010/0160876 A1 | 6/2010 | Robinson et al. |
| 2010/0179515 A1 | 7/2010 | Swain et al. |
| 2010/0191178 A1 | 7/2010 | Ross et al. |
| 2010/0198128 A1 | 8/2010 | Turnlund et al. |
| 2010/0211030 A1 | 8/2010 | Turner et al. |
| 2010/0222645 A1 | 9/2010 | Nadler et al. |
| 2010/0234708 A1 | 9/2010 | Buck et al. |
| 2010/0255876 A1 | 10/2010 | Jordan et al. |
| 2010/0256672 A1 | 10/2010 | Weinberg et al. |
| 2010/0262092 A1 | 10/2010 | Hartwell |
| 2010/0262126 A1 | 10/2010 | Hu et al. |
| 2010/0280435 A1 | 11/2010 | Raney et al. |
| 2010/0280536 A1 | 11/2010 | Hartwell |
| 2010/0292717 A1 | 11/2010 | Petter-Puchner et al. |
| 2010/0305523 A1 | 12/2010 | Vess |
| 2010/0312159 A1 | 12/2010 | Aali et al. |
| 2010/0318043 A1 | 12/2010 | Malhi et al. |
| 2010/0318071 A1 | 12/2010 | Wudyka |
| 2011/0004188 A1 | 1/2011 | Shekalim |
| 2011/0009838 A1 | 1/2011 | Greener |
| 2011/0015587 A1 | 1/2011 | Tumey et al. |
| 2011/0021965 A1 | 1/2011 | Karp et al. |
| 2011/0022082 A1 | 1/2011 | Burke et al. |
| 2011/0038741 A1 | 2/2011 | Lissner et al. |
| 2011/0054810 A1 | 3/2011 | Turner et al. |
| 2011/0059291 A1 | 3/2011 | Boyce et al. |
| 2011/0060204 A1 | 3/2011 | Weston |
| 2011/0063117 A1 | 3/2011 | Turner et al. |
| 2011/0066096 A1 | 3/2011 | Svedman |
| 2011/0066110 A1 | 3/2011 | Fathallah et al. |
| 2011/0071415 A1 | 3/2011 | Karwoski et al. |
| 2011/0071844 A1 | 3/2011 | Cannon et al. |
| 2011/0073107 A1 | 3/2011 | Rodman et al. |
| 2011/0082480 A1 | 4/2011 | Viola |
| 2011/0092927 A1 | 4/2011 | Wilkes et al. |
| 2011/0106026 A1 | 5/2011 | Wu et al. |
| 2011/0106028 A1 | 5/2011 | Giezendanner et al. |
| 2011/0106561 A1 | 5/2011 | Eaton, Jr. et al. |
| 2011/0110996 A1 | 5/2011 | Schoenberger et al. |
| 2011/0112458 A1 | 5/2011 | Holm et al. |
| 2011/0130712 A1 | 6/2011 | Topaz |
| 2011/0130774 A1 | 6/2011 | Criscuolo et al. |
| 2011/0137759 A1 | 6/2011 | Wellington et al. |
| 2011/0145018 A1 | 6/2011 | Fotsch et al. |
| 2011/0152800 A1 | 6/2011 | Eckstein et al. |
| 2011/0172760 A1 | 7/2011 | Anderson |
| 2011/0173028 A1 | 7/2011 | Bond |
| 2011/0178451 A1 | 7/2011 | Robinson et al. |
| 2011/0184754 A1 | 7/2011 | Park et al. |
| 2011/0196321 A1 | 8/2011 | Wudyka |
| 2011/0213319 A1 | 9/2011 | Blott et al. |
| 2011/0224631 A1 | 9/2011 | Simmons et al. |
| 2011/0224634 A1 | 9/2011 | Locke et al. |
| 2011/0225008 A1 | 9/2011 | Elkouh et al. |
| 2011/0236460 A1 | 9/2011 | Stopek et al. |
| 2011/0238095 A1 | 9/2011 | Browning |
| 2011/0246219 A1 | 10/2011 | Smith et al. |
| 2011/0251569 A1 | 10/2011 | Turner et al. |
| 2011/0257572 A1 | 10/2011 | Locke et al. |
| 2011/0264138 A1 | 10/2011 | Avelar et al. |
| 2011/0275353 A1 | 11/2011 | Liu |
| 2011/0282136 A1 | 11/2011 | Browning |
| 2011/0282309 A1 | 11/2011 | Adie et al. |
| 2011/0288878 A1 | 11/2011 | Blair |
| 2011/0305736 A1 | 12/2011 | Wieland et al. |
| 2012/0001762 A1 | 1/2012 | Turner et al. |
| 2012/0004631 A9 | 1/2012 | Hartwell |
| 2012/0010637 A1 | 1/2012 | Stopek et al. |
| 2012/0029312 A1 | 2/2012 | Beaudry et al. |
| 2012/0029313 A1 | 2/2012 | Burdett et al. |
| 2012/0029449 A1 | 2/2012 | Khosrowshahi |
| 2012/0029455 A1 | 2/2012 | Perez-Foullerat et al. |
| 2012/0032819 A1 | 2/2012 | Chae et al. |
| 2012/0035427 A1 | 2/2012 | Friedman et al. |
| 2012/0035560 A1 | 2/2012 | Eddy et al. |
| 2012/0046625 A1 | 2/2012 | Johannison |
| 2012/0059399 A1 | 3/2012 | Hoke et al. |
| 2012/0059412 A1 | 3/2012 | Fleischmann |
| 2012/0071841 A1 | 3/2012 | Bengtson |
| 2012/0077605 A1 | 3/2012 | Nakagaito et al. |
| 2012/0081225 A1 | 4/2012 | Waugh et al. |
| 2012/0089369 A1 | 4/2012 | Abuzeni et al. |
| 2012/0109188 A1 | 5/2012 | Viola |
| 2012/0121556 A1 | 5/2012 | Fraser et al. |
| 2012/0123323 A1 | 5/2012 | Kagan et al. |
| 2012/0123358 A1 | 5/2012 | Hall et al. |
| 2012/0123796 A1 | 5/2012 | McFaul |
| 2012/0130327 A1 | 5/2012 | Marquez |
| 2012/0136326 A1 | 5/2012 | Croizat et al. |
| 2012/0136328 A1 | 5/2012 | Johannison et al. |
| 2012/0143113 A1 | 6/2012 | Robinson et al. |
| 2012/0144989 A1 | 6/2012 | Du Plessis et al. |
| 2012/0157889 A1 | 6/2012 | Tanis et al. |
| 2012/0165764 A1 | 6/2012 | Allen et al. |
| 2012/0172926 A1 | 7/2012 | Hotter |
| 2012/0181405 A1 | 7/2012 | Zlatic et al. |
| 2012/0182143 A1 | 7/2012 | Gaines et al. |
| 2012/0184930 A1 | 7/2012 | Johannison |
| 2012/0184932 A1 | 7/2012 | Giezendanner et al. |
| 2012/0191132 A1 | 7/2012 | Sargeant |
| 2012/0191475 A1 | 7/2012 | Pandey |
| 2012/0197415 A1 | 8/2012 | Montanari et al. |
| 2012/0209226 A1 | 8/2012 | Simmons et al. |
| 2012/0209227 A1 | 8/2012 | Dunn |

(56) References Cited

U.S. PATENT DOCUMENTS

| | | |
|---|---|---|
| 2012/0212455 A1 | 8/2012 | Kloeffel |
| 2012/0215455 A1 | 8/2012 | Patil et al. |
| 2012/0220960 A1 | 8/2012 | Ruland |
| 2012/0226247 A1 | 9/2012 | Danei et al. |
| 2012/0238931 A1 | 9/2012 | Rastegar et al. |
| 2012/0253302 A1 | 10/2012 | Corley |
| 2012/0259283 A1 | 10/2012 | Haase |
| 2012/0259651 A1 | 10/2012 | Mallon et al. |
| 2012/0271256 A1 | 10/2012 | Locke et al. |
| 2012/0277773 A1 | 11/2012 | Sargeant et al. |
| 2012/0289895 A1 | 11/2012 | Tsoukalis |
| 2012/0289913 A1 | 11/2012 | Eckstein et al. |
| 2012/0290217 A1 | 11/2012 | Shoval et al. |
| 2012/0295566 A1 | 11/2012 | Collins et al. |
| 2012/0310205 A1 | 12/2012 | Lee et al. |
| 2013/0012891 A1 | 1/2013 | Gross et al. |
| 2013/0018355 A1 | 1/2013 | Brand et al. |
| 2013/0023842 A1 | 1/2013 | Song |
| 2013/0035615 A1 | 2/2013 | Hsieh |
| 2013/0045764 A1 | 2/2013 | Vik et al. |
| 2013/0066365 A1 | 3/2013 | Belson et al. |
| 2013/0073303 A1 | 3/2013 | Hsu |
| 2013/0076528 A1 | 3/2013 | Boettner et al. |
| 2013/0087609 A1 | 4/2013 | Nichol et al. |
| 2013/0090949 A1 | 4/2013 | Tibebu |
| 2013/0096518 A1 | 4/2013 | Hall et al. |
| 2013/0103419 A1 | 4/2013 | Beaudry |
| 2013/0110058 A1 | 5/2013 | Adie et al. |
| 2013/0110066 A1 | 5/2013 | Sharma et al. |
| 2013/0124227 A1 | 5/2013 | Ellis |
| 2013/0131564 A1 | 5/2013 | Locke et al. |
| 2013/0132855 A1 | 5/2013 | Manicka et al. |
| 2013/0144227 A1 | 6/2013 | Locke et al. |
| 2013/0150686 A1 | 6/2013 | Fronterhouse et al. |
| 2013/0150698 A1 | 6/2013 | Hsu et al. |
| 2013/0150813 A1 | 6/2013 | Gordon et al. |
| 2013/0150814 A1 | 6/2013 | Buan |
| 2013/0151274 A1 | 6/2013 | Bage et al. |
| 2013/0157571 A1 | 6/2013 | Wondka et al. |
| 2013/0159456 A1 | 6/2013 | Daoud et al. |
| 2013/0160082 A1 | 6/2013 | Miller |
| 2013/0165877 A1 | 6/2013 | Leeson et al. |
| 2013/0186405 A1 | 7/2013 | Krzyzanowski et al. |
| 2013/0190705 A1 | 7/2013 | Vess et al. |
| 2013/0190903 A1 | 7/2013 | Balakrishnan et al. |
| 2013/0191513 A1 | 7/2013 | Kamen et al. |
| 2013/0196703 A1 | 8/2013 | Masoud et al. |
| 2013/0204106 A1 | 8/2013 | Bennett |
| 2013/0204213 A1 | 8/2013 | Heagle et al. |
| 2013/0211206 A1 | 8/2013 | Sands et al. |
| 2013/0211854 A1 | 8/2013 | Wagstaff |
| 2013/0212168 A1 | 8/2013 | Bonasera et al. |
| 2013/0214925 A1 | 8/2013 | Weiss |
| 2013/0218053 A1 | 8/2013 | Kaiser et al. |
| 2013/0226607 A1 | 8/2013 | Woody et al. |
| 2013/0227128 A1 | 8/2013 | Wagstaff |
| 2013/0231596 A1 | 9/2013 | Hornbach et al. |
| 2013/0245387 A1 | 9/2013 | Patel |
| 2013/0245527 A1 | 9/2013 | Croizat et al. |
| 2013/0253952 A1 | 9/2013 | Burke et al. |
| 2013/0255681 A1 | 10/2013 | Batch et al. |
| 2013/0267918 A1 | 10/2013 | Pan et al. |
| 2013/0267919 A1 | 10/2013 | Caso et al. |
| 2013/0268283 A1 | 10/2013 | Vann et al. |
| 2013/0271556 A1 | 10/2013 | Ross et al. |
| 2013/0285837 A1 | 10/2013 | Uchida |
| 2013/0297350 A1 | 11/2013 | Gross et al. |
| 2013/0304489 A1 | 11/2013 | Miller |
| 2013/0310726 A1 | 11/2013 | Miller et al. |
| 2013/0317753 A1 | 11/2013 | Kamen et al. |
| 2013/0325142 A1 | 12/2013 | Hunter et al. |
| 2013/0325508 A1 | 12/2013 | Johnson et al. |
| 2013/0331748 A1 | 12/2013 | Wright et al. |
| 2013/0331757 A1 | 12/2013 | Belson |
| 2013/0332197 A1 | 12/2013 | Hinkel |
| 2013/0335233 A1 | 12/2013 | Kamar et al. |
| 2013/0339049 A1 | 12/2013 | Blumberg, Jr. et al. |
| 2013/0345524 A1 | 12/2013 | Meyer et al. |
| 2014/0002234 A1 | 1/2014 | Alwan |
| 2014/0028464 A1 | 1/2014 | Garibaldi |
| 2014/0031884 A1 | 1/2014 | Elghazzawi |
| 2014/0032231 A1 | 1/2014 | Semen et al. |
| 2014/0058714 A1 | 2/2014 | Boyer |
| 2014/0087762 A1 | 3/2014 | Galvin et al. |
| 2014/0094730 A1 | 4/2014 | Greener et al. |
| 2014/0100516 A1 | 4/2014 | Hunt et al. |
| 2014/0108033 A1 | 4/2014 | Akbay et al. |
| 2014/0108034 A1 | 4/2014 | Akbay et al. |
| 2014/0108035 A1 | 4/2014 | Akbay et al. |
| 2014/0109560 A1 | 4/2014 | Ilievski et al. |
| 2014/0114236 A1 | 4/2014 | Gordon |
| 2014/0114237 A1 | 4/2014 | Gordon |
| 2014/0129250 A1 | 5/2014 | Daniel et al. |
| 2014/0148138 A1 | 5/2014 | Chou |
| 2014/0163415 A1 | 6/2014 | Zaiken et al. |
| 2014/0163490 A1 | 6/2014 | Locke et al. |
| 2014/0171753 A1 | 6/2014 | Montejo et al. |
| 2014/0180225 A1 | 6/2014 | Dunn |
| 2014/0180229 A1 | 6/2014 | Fuller et al. |
| 2014/0187888 A1 | 7/2014 | Hatziantoniou |
| 2014/0194835 A1 | 7/2014 | Ehlert |
| 2014/0195004 A9 | 7/2014 | Engqvist et al. |
| 2014/0207090 A1 | 7/2014 | Jian |
| 2014/0222446 A1 | 8/2014 | Ash et al. |
| 2014/0235975 A1 | 8/2014 | Carnes |
| 2014/0244285 A1 | 8/2014 | Hinkle et al. |
| 2014/0244301 A1 | 8/2014 | Lee et al. |
| 2014/0244307 A1 | 8/2014 | Shutko et al. |
| 2014/0249495 A1 | 9/2014 | Mumby et al. |
| 2014/0266713 A1 | 9/2014 | Sehgal et al. |
| 2014/0275876 A1 | 9/2014 | Hansen et al. |
| 2014/0278502 A1 | 9/2014 | Laskin |
| 2014/0280882 A1 | 9/2014 | Lacerte et al. |
| 2014/0297299 A1 | 10/2014 | Lester, IV |
| 2014/0303551 A1 | 10/2014 | Germain et al. |
| 2014/0316359 A1 | 10/2014 | Collinson et al. |
| 2014/0316819 A1 | 10/2014 | Dunsirn et al. |
| 2014/0323906 A1 | 10/2014 | Peatfield et al. |
| 2014/0343518 A1 | 11/2014 | Riesinger |
| 2014/0366878 A1 | 12/2014 | Baron |
| 2015/0012290 A1 | 1/2015 | Inciardi et al. |
| 2015/0025486 A1 | 1/2015 | Hu et al. |
| 2015/0065968 A1 | 3/2015 | Sealy et al. |
| 2015/0094830 A1 | 4/2015 | Lipoma et al. |
| 2015/0112311 A1 | 4/2015 | Hammond et al. |
| 2015/0119837 A1 | 4/2015 | Thompson, Jr. et al. |
| 2015/0148760 A1 | 5/2015 | Dodd et al. |
| 2015/0157758 A1 | 6/2015 | Blucher et al. |
| 2015/0159066 A1 | 6/2015 | Hartwell et al. |
| 2015/0174304 A1 | 6/2015 | Askem et al. |
| 2015/0186615 A1 | 7/2015 | Armor et al. |
| 2015/0189001 A1 | 7/2015 | Lee et al. |
| 2015/0196431 A1 | 7/2015 | Dunn et al. |
| 2015/0216732 A1 | 8/2015 | Hartwell et al. |
| 2015/0234995 A1 | 8/2015 | Casady et al. |
| 2015/0242578 A1 | 8/2015 | Siemon |
| 2015/0363058 A1 | 12/2015 | Chung et al. |
| 2015/0370984 A1 | 12/2015 | Russell et al. |
| 2016/0018963 A1 | 1/2016 | Robbins et al. |
| 2016/0030646 A1 | 2/2016 | Hartwell et al. |
| 2016/0042154 A1 | 2/2016 | Goldberg et al. |
| 2016/0044141 A1 | 2/2016 | Pfützenreuter et al. |
| 2016/0055310 A1 | 2/2016 | Bentley et al. |
| 2016/0063210 A1 | 3/2016 | Bardi et al. |
| 2016/0080365 A1 | 3/2016 | Baker et al. |
| 2016/0110507 A1 | 4/2016 | Abbo |
| 2016/0151015 A1 | 6/2016 | Condurso et al. |
| 2016/0154936 A1 | 6/2016 | Kalathil |
| 2016/0166744 A1 | 6/2016 | Hartwell et al. |
| 2016/0171866 A1 | 6/2016 | Dupasquier et al. |
| 2016/0203275 A1 | 7/2016 | Benjamin et al. |
| 2016/0321422 A1 | 11/2016 | Albright |
| 2017/0065751 A1 | 3/2017 | Toth |
| 2017/0150939 A1 | 6/2017 | Shah |

(56) References Cited

U.S. PATENT DOCUMENTS

| | | | |
|---|---|---|---|
| 2017/0156611 | A1 | 6/2017 | Burnett et al. |
| 2017/0273116 | A1 | 9/2017 | Elghazzawi |
| 2018/0139572 | A1 | 5/2018 | Hansen |
| 2018/0158545 | A1 | 6/2018 | Blomquist |
| 2018/0233016 | A1 | 8/2018 | Daniel et al. |
| 2018/0233221 | A1 | 8/2018 | Blomquist |

FOREIGN PATENT DOCUMENTS

| | | |
|---|---|---|
| CN | 101112326 A | 1/2008 |
| CN | 101744688 A | 6/2010 |
| CN | 201519362 U | 7/2010 |
| CN | 102038575 A | 5/2011 |
| CN | 202568632 U | 12/2012 |
| CN | 102961815 A | 3/2013 |
| CN | 103071197 A | 5/2013 |
| DE | 2949920 A1 | 3/1981 |
| DE | 102010036405 A1 | 1/2012 |
| EP | 0980227 A1 | 2/2000 |
| EP | 0566381 B1 | 7/2002 |
| EP | 1231965 A2 | 8/2002 |
| EP | 1291802 A2 | 3/2003 |
| EP | 1309960 A1 | 5/2003 |
| EP | 1320342 A1 | 6/2003 |
| EP | 0814864 B1 | 12/2003 |
| EP | 1407624 A2 | 4/2004 |
| EP | 1011420 B1 | 12/2004 |
| EP | 1495713 A1 | 1/2005 |
| EP | 1524619 A2 | 4/2005 |
| EP | 1540557 A2 | 6/2005 |
| EP | 1579367 A2 | 9/2005 |
| EP | 1587017 A2 | 10/2005 |
| EP | 1788503 A2 | 5/2007 |
| EP | 1839244 A1 | 10/2007 |
| EP | 1839615 A1 | 10/2007 |
| EP | 1857950 A2 | 11/2007 |
| EP | 1870068 A1 | 12/2007 |
| EP | 1904964 A1 | 4/2008 |
| EP | 1934852 A1 | 6/2008 |
| EP | 1975828 A2 | 10/2008 |
| EP | 1993435 A2 | 11/2008 |
| EP | 2038786 A2 | 3/2009 |
| EP | 2040604 A2 | 4/2009 |
| EP | 2092470 A2 | 8/2009 |
| EP | 2146297 A1 | 1/2010 |
| EP | 2172859 A1 | 4/2010 |
| EP | 2214552 A1 | 8/2010 |
| EP | 2218478 A1 | 8/2010 |
| EP | 1404213 B1 | 3/2011 |
| EP | 1247229 B1 | 4/2011 |
| EP | 1406540 B1 | 6/2011 |
| EP | 1812094 B1 | 8/2011 |
| EP | 2366721 A1 | 9/2011 |
| EP | 2384472 A1 | 11/2011 |
| EP | 2226002 B1 | 1/2012 |
| EP | 2404626 A2 | 1/2012 |
| EP | 1610494 B1 | 3/2012 |
| EP | 1248660 B1 | 4/2012 |
| EP | 2023800 B1 | 4/2012 |
| EP | 2451513 A1 | 5/2012 |
| EP | 1248661 B1 | 8/2012 |
| EP | 2488977 A1 | 8/2012 |
| EP | 2547375 A1 | 1/2013 |
| EP | 2562665 A2 | 2/2013 |
| EP | 2567717 A1 | 3/2013 |
| EP | 2619723 A2 | 7/2013 |
| EP | 1881784 B1 | 10/2013 |
| EP | 2664194 A2 | 11/2013 |
| EP | 2743850 A2 | 6/2014 |
| EP | 2745204 A1 | 6/2014 |
| EP | 1684146 B1 | 7/2014 |
| EP | 2841895 A1 | 3/2015 |
| EP | 2850771 A1 | 3/2015 |
| EP | 2906101 A2 | 8/2015 |
| EP | 2962266 A1 | 1/2016 |
| EP | 2968829 A1 | 1/2016 |
| EP | 2973089 A1 | 1/2016 |
| EP | 2563437 B1 | 3/2017 |
| EP | 2556650 B1 | 5/2017 |
| EP | 2632407 B1 | 8/2017 |
| EP | 2856767 B1 | 11/2017 |
| EP | 2320971 B1 | 5/2018 |
| EP | 2335173 B1 | 5/2018 |
| EP | 2440112 B1 | 10/2018 |
| EP | 2992500 B1 | 12/2018 |
| EP | 2597584 B1 | 1/2019 |
| EP | 3219340 B1 | 1/2019 |
| EP | 2890456 B1 | 2/2019 |
| EP | 2836269 B1 | 8/2019 |
| EP | 2866851 B1 | 9/2019 |
| GB | 2235877 A | 3/1991 |
| GB | 2389794 A | 12/2003 |
| GB | 2378392 B | 6/2004 |
| GB | 2409951 A | 7/2005 |
| GB | 2423019 A | 8/2006 |
| GB | 2436160 A | 9/2007 |
| GB | 2449400 A | 11/2008 |
| GB | 2456708 A | 7/2009 |
| GB | 2423178 B | 5/2010 |
| GB | 2475091 A | 5/2011 |
| GB | 2488904 A | 9/2012 |
| GB | 2489947 A | 10/2012 |
| GB | 2446923 B | 5/2013 |
| GB | 2496310 A | 5/2013 |
| GB | 2499986 A | 9/2013 |
| GB | 2491946 B | 8/2014 |
| GB | 2499873 B | 5/2016 |
| JP | S6257560 A | 3/1987 |
| JP | H0341952 A | 2/1991 |
| JP | 2006528038 A | 12/2006 |
| JP | 2009525087 A | 7/2009 |
| JP | 2011521740 A | 7/2011 |
| JP | 2012105840 A | 6/2012 |
| JP | 2012529974 A | 11/2012 |
| JP | 2014168573 A | 9/2014 |
| RU | 1818103 A1 | 5/1993 |
| RU | 62504 U1 | 4/2007 |
| WO | WO-9619335 A1 | 6/1996 |
| WO | WO-9627163 A1 | 9/1996 |
| WO | WO-9744745 A1 | 11/1997 |
| WO | WO-9924927 A1 | 5/1999 |
| WO | WO-9963886 A1 | 12/1999 |
| WO | WO-0032088 A1 | 6/2000 |
| WO | WO-0060522 A2 | 10/2000 |
| WO | WO-0133457 A1 | 5/2001 |
| WO | WO-0181829 A1 | 11/2001 |
| WO | WO-0205737 A1 | 1/2002 |
| WO | WO-0217075 A2 | 2/2002 |
| WO | WO-0233577 A1 | 4/2002 |
| WO | WO-02078594 A2 | 10/2002 |
| WO | WO-02101713 A1 | 12/2002 |
| WO | WO-03003948 A1 | 1/2003 |
| WO | WO-03049598 A2 | 6/2003 |
| WO | WO-03054668 A2 | 7/2003 |
| WO | WO-03101508 A2 | 12/2003 |
| WO | WO-2004057514 A2 | 7/2004 |
| WO | WO-2004074457 A2 | 9/2004 |
| WO | WO-2005022349 A2 | 3/2005 |
| WO | WO-2005031632 A2 | 4/2005 |
| WO | WO-2005036447 A2 | 4/2005 |
| WO | WO-2005045461 A1 | 5/2005 |
| WO | WO-2005046761 A1 | 5/2005 |
| WO | WO-2005053793 A1 | 6/2005 |
| WO | WO-2005057466 A2 | 6/2005 |
| WO | WO-2005083619 A2 | 9/2005 |
| WO | WO-2005101282 A2 | 10/2005 |
| WO | WO-2005105174 A1 | 11/2005 |
| WO | WO-2005109297 A2 | 11/2005 |
| WO | WO-2005120097 A2 | 12/2005 |
| WO | WO-2006021154 A1 | 3/2006 |
| WO | WO-2006041496 A1 | 4/2006 |
| WO | WO-2006066583 A1 | 6/2006 |
| WO | WO-2006066585 A2 | 6/2006 |
| WO | WO-2006071711 A2 | 7/2006 |

(56) References Cited

FOREIGN PATENT DOCUMENTS

| | | |
|---|---|---|
| WO | WO-2006099120 A2 | 9/2006 |
| WO | WO-2006108304 A1 | 10/2006 |
| WO | WO-2006108858 A1 | 10/2006 |
| WO | WO-2006111109 A1 | 10/2006 |
| WO | WO-2007027490 A2 | 3/2007 |
| WO | WO-2007035646 A2 | 3/2007 |
| WO | WO-2007127879 A2 | 11/2007 |
| WO | WO-2007133478 A2 | 11/2007 |
| WO | WO-2007137869 A2 | 12/2007 |
| WO | WO-2008010012 A2 | 1/2008 |
| WO | WO-2008027449 A2 | 3/2008 |
| WO | WO-2008036344 A1 | 3/2008 |
| WO | WO-2008062382 A2 | 5/2008 |
| WO | WO-2008064502 A1 | 6/2008 |
| WO | WO-2008104609 A1 | 9/2008 |
| WO | WO-2008116295 A1 | 10/2008 |
| WO | WO-2008150633 A2 | 12/2008 |
| WO | WO-2009019495 A1 | 2/2009 |
| WO | WO-2009071926 A1 | 6/2009 |
| WO | WO-2009071933 A2 | 6/2009 |
| WO | WO-2009112062 A1 | 9/2009 |
| WO | WO-2009140669 A2 | 11/2009 |
| WO | WO-2009156709 A1 | 12/2009 |
| WO | WO-2010025166 A1 | 3/2010 |
| WO | WO-2010025467 A1 | 3/2010 |
| WO | WO-2010078558 A1 | 7/2010 |
| WO | WO-2010085033 A2 | 7/2010 |
| WO | WO-2010097570 A1 | 9/2010 |
| WO | WO-2010132617 A2 | 11/2010 |
| WO | WO-2010145780 A1 | 12/2010 |
| WO | WO-2011005633 A2 | 1/2011 |
| WO | WO-2011023384 A1 | 3/2011 |
| WO | WO-2011039676 A2 | 4/2011 |
| WO | WO-2011046860 A2 | 4/2011 |
| WO | WO-2011047334 A1 | 4/2011 |
| WO | WO-2011087871 A2 | 7/2011 |
| WO | WO-2011091169 A1 | 7/2011 |
| WO | WO-2011107972 A1 | 9/2011 |
| WO | WO-2011124388 A1 | 10/2011 |
| WO | WO-2011137230 A1 | 11/2011 |
| WO | WO-2012009869 A1 | 1/2012 |
| WO | WO-2012027913 A1 | 3/2012 |
| WO | WO-2012027914 A1 | 3/2012 |
| WO | WO-2012027915 A1 | 3/2012 |
| WO | WO-2012027916 A1 | 3/2012 |
| WO | WO-2012038727 A2 | 3/2012 |
| WO | WO-2012069793 A1 | 5/2012 |
| WO | WO-2012082716 A2 | 6/2012 |
| WO | WO-2012082876 A1 | 6/2012 |
| WO | WO-2012127281 A1 | 9/2012 |
| WO | WO-2012136707 A1 | 10/2012 |
| WO | WO-2012142473 A1 | 10/2012 |
| WO | WO-2012156655 A1 | 11/2012 |
| WO | WO-2012168678 A1 | 12/2012 |
| WO | WO-2013012381 A1 | 1/2013 |
| WO | WO-2013026999 A1 | 2/2013 |
| WO | WO-2013036853 A2 | 3/2013 |
| WO | WO-2013043258 A1 | 3/2013 |
| WO | WO-2013061887 A1 | 5/2013 |
| WO | WO-2013063848 A1 | 5/2013 |
| WO | WO-2013071243 A2 | 5/2013 |
| WO | WO-2013079447 A1 | 6/2013 |
| WO | WO-2013079947 A1 | 6/2013 |
| WO | WO-2013102855 A1 | 7/2013 |
| WO | WO-2013109517 A1 | 7/2013 |
| WO | WO-2013138182 A1 | 9/2013 |
| WO | WO-2013141870 A1 | 9/2013 |
| WO | WO-2013155193 A1 | 10/2013 |
| WO | WO-2013175076 A1 | 11/2013 |
| WO | WO-2014014922 A1 * | 1/2014 ....... A61F 13/00068 |
| WO | WO-2014015215 A2 | 1/2014 |
| WO | WO-2014018786 A2 | 1/2014 |
| WO | WO-2014075494 A1 | 5/2014 |
| WO | WO-2014089086 A1 | 6/2014 |
| WO | WO-2014100036 A1 | 6/2014 |
| WO | WO-2014106056 A2 | 7/2014 |
| WO | WO-2014123846 A1 | 8/2014 |
| WO | WO-2014133822 A2 | 9/2014 |
| WO | WO-2014141221 A2 | 9/2014 |
| WO | WO-2014145496 A1 | 9/2014 |
| WO | WO-2014150255 A2 | 9/2014 |
| WO | WO-2014152963 A1 | 9/2014 |
| WO | WO-2014158526 A1 | 10/2014 |
| WO | WO-2014178945 A1 | 11/2014 |
| WO | WO-2014189070 A1 | 11/2014 |
| WO | WO-2014009876 A3 | 12/2014 |

OTHER PUBLICATIONS

"Definition of Adhere," The Free Dictionary, accessed on Mar. 23, 2017 from http://www.thefreedictionary.com/adhere, 6 pages.
"Definition of Oculiform," Webster's Revised Unabridged Dictionary, accessed from The Free Dictionary on May 30, 2018 from URL: https://www.thefreedictionary.com/Oculiform, 1913, 1 page.
"Definition of Throughout," Merriam-Webster Dictionary, accessed on Aug. 29, 2017 from https://www.merriam-webster.com/dictionary/throughout, 11 pages.
Hartmann Vivano., "Vivano—Product Application Description," retrieved from http://www.vivanosystem.info/20809.php, accessed on Feb. 28, 2013, 3 pages.
International Preliminary Report on Patentability for Application No. PCT/IB2013/001562, mailed on Nov. 25, 2014, 9 pages.
International Search Report for Application No. PCT/IB2013/001562, mailed on Mar. 21, 2014, 7 pages.
Invitation to Pay Additional Fees and Partial Search Report for Application No. PCT/IB2013/001562, mailed on Nov. 15, 2013, 75 pages.
Kapischke M., et al., "Self-Fixating Mesh for the Lichtenstein Procedure—a Prestudy," Langenbecks Arch Surg, 2010, vol. 395, pp. 317-322.

* cited by examiner

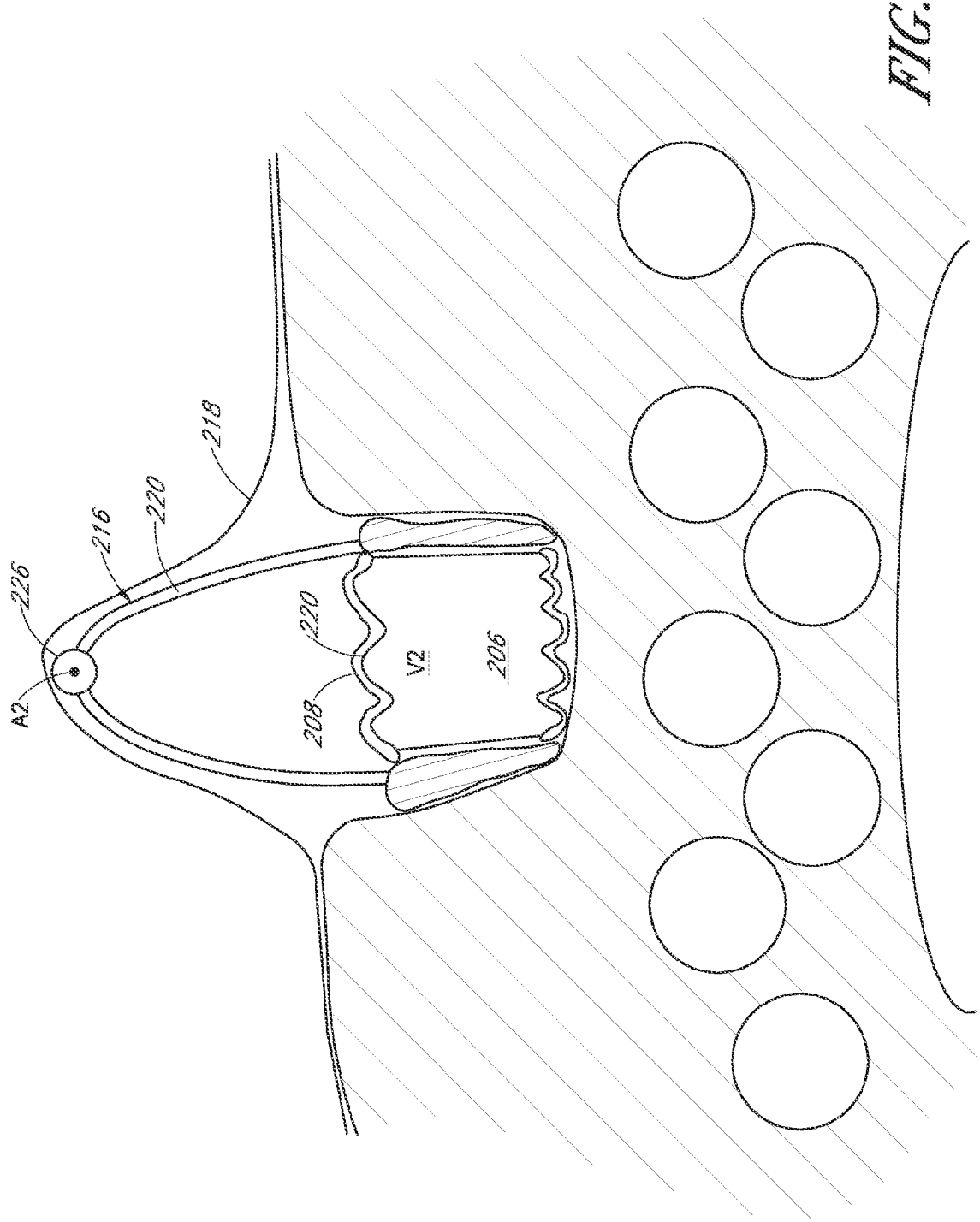

APPARATUSES AND METHODS FOR WOUND THERAPY

CROSS-REFERENCE TO RELATED APPLICATIONS

This application is a continuation of U.S. application Ser. No. 16/105,852, filed Aug. 20, 2018, which is a continuation of U.S. patent application Ser. No. 14/402,976, filed Nov. 21, 2014, which is a national stage application of International Patent Application No. PCT/IB2013/001562, filed May 21, 2013, which claims the benefit of U.S. Provisional Application Nos. 61/650,391, filed May 22, 2012, entitled WOUND CLOSURE DEVICE, 61/663,405, filed Jun. 22, 2012, entitled APPARATUSES AND METHODS FOR VISUALIZATION OF TISSUE INTERFACE, 61/681,037, filed Aug. 8, 2012, entitled WOUND CLOSURE DEVICE, and 61/782,026, filed Mar. 14, 2013, entitled WOUND CLOSURE DEVICE, the contents of which are hereby incorporated by reference in their entireties as if fully set forth herein. The benefit of priority to the foregoing applications is claimed under the appropriate legal basis including, without limitation, under 35 U.S.C. § 119(e).

BACKGROUND OF THE DISCLOSURE

Field of the Disclosure

Embodiments or arrangements disclosed herein relate to methods and apparatuses for visualizing a position of a wound interface or a degree of closure of a wound. Such apparatuses and methods can be applied to a wide range of wounds, for example an abdominal wound or following fasciotomy procedures. The methods and apparatuses for visualizing a position of a wound interface or a degree of closure of a wound may be used with topical negative pressure (TNP) therapy dressings or kits, but are not required to be. Other embodiments disclosed herein relate to methods and apparatuses for treating a wound with negative pressure, and for detecting excessive compartment pressures and adjusting treatment to reduce such excessive pressures.

Description of the Related Art

A number of techniques have been developed for treatment (e.g., closure) of wounds, including wounds resulting from accident and wounds resulting from surgery. Often, for deeper wounds in the abdominal region, fasciotomy procedures on deep tissue, deep trauma wounds, or pressure ulcers, it is difficult or impossible to determine whether the deeper layers of tissue are being drawn together by the surgical or wound therapy treatment methods. It is particularly difficult to determine if the deeper layers of tissue, such as the subcutaneous, muscle and fascial layer, are closing or have closed during wound closure treatment after an open abdominal surgical procedure or fasciotomy.

The application of reduced or negative pressure to a wound site has been found to generally promote faster healing, increased blood flow, decreased bacterial burden, increased rate of granulation tissue formation, to stimulate the proliferation of fibroblasts, stimulate the proliferation of endothelial cells, close chronic open wounds, inhibit burn penetration, and/or enhance flap and graft attachment, among other things. It has also been reported that wounds that have exhibited positive response to treatment by the application of negative pressure include infected open wounds, decubitus ulcers, dehisced incisions, partial thickness burns, and various lesions to which flaps or grafts have been attached. Consequently, the application of negative pressure to a wound site can be beneficial to a patient.

Compartment syndrome can occur when excessive pressure builds up inside an enclosed space in the body. Excessive pressures in the abdominal compartment, for example, can impede the flow of blood to and from the affected tissues, bodily organs, or even the lower extremities if excessive pressure is exerted on the abdominal aorta. The pressure buildup within the abdominal compartment can be the result of excessive fluid buildup in the abdominal compartment, in addition to or alternatively as a result of the forces exerted on the abdominal region from the application of negative pressure wound therapy to the abdominal compartment. Such excessive pressure can cause permanent injury or damage to the tissues, organs (such as the liver, bowels, kidneys, and other organs), and other body parts affected by the reduction of blood flow.

SUMMARY OF SOME EMBODIMENTS

Some embodiments of the present disclosure relate to visualization apparatuses and methods for visualizing a position of a wound interface during negative pressure wound therapy. Some embodiments of the present disclosure relate to pressure sensing, feedback, and control systems for preventing compartment syndrome during application of negative pressure wound therapy or any therapeutic treatment of wounds. Other embodiments of the present disclosure relate to methods and apparatuses for controlling the rate of closure of a wound.

Any of the features, components, or details of any of the arrangements or embodiments disclosed in this application, including those disclosed below, are interchangeably combinable with any other features, components, or details of any of the arrangements or embodiments disclosed herein to form new arrangements and embodiments. With that, the following are examples of arrangements disclosed herein.

1. A visualization element to visualize a location of a wound surface, comprising:
   a radiopaque member that is configured to be positioned on or adjacent to a surface of an open wound.

2. The visualization element of arrangement 1, wherein the visualization element comprises a radiopaque marker, the radiopaque marker being configured to be attached to an edge or the surface of the wound.

3. The visualization element of any one of the previous arrangements, wherein the visualization element comprises a radiopaque marker configured to be attached to the surface of the wound along at least one of subdermal layer, a fat layer, a muscle layer, and a fascia layer.

4. The visualization element of any one of the previous arrangements, wherein the visualization element comprises a radiopaque marker configured to be attached to the surface of the wound along the fascia layer and at least one of subdermal layer, a fat layer, and a muscle layer.

5. The visualization element of any one of the previous arrangements, comprising a plurality of radiopaque markers configured to be attached to the surface of the wound.

6. The visualization element of any one of the previous arrangements, wherein the visualization element comprises a gold wire that is configured to be advanced through tissue at the surface of the wound.

7. The visualization element of any one of the previous arrangements, wherein the visualization element comprises a suture wire that is configured to be advanced through tissue at the surface of the wound, the suture wire comprising at least one of barium sulfate, zirconium, gold, titanium, and tungsten oxide.

8. The visualization element of any one of the previous arrangements, wherein the visualization element comprises a suture wire that is configured to be stitched through tissue at the surface of the wound in a running stitch and/or a loop stitch.

9. The visualization element of any one of the previous arrangements, wherein the visualization element comprises a gold wire that is configured to be advanced through the peritoneum tissue at and/or adjacent to the surface of the wound.

10. The visualization element of any one of the previous arrangements, wherein the visualization element comprises a bioabsorbable material.

11. The visualization element of any one of the previous arrangements, wherein the visualization element comprises an adhesive configured to be applied to a surface of the wound, the adhesive comprising a radiopaque material.

12. The visualization element of arrangement 11, wherein the radiopaque material comprises at least one of least one of barium sulfate, zirconium, gold, titanium, and tungsten oxide.

13. A kit for use in the treatment of a wound using negative pressure wound therapy, the kit comprising:
   the visualization element of any one of the previous arrangements configured to be positioned on or adjacent to a surface of an open wound;
   a dressing configured to sealably cover the wound; and
   a source of negative pressure configured to apply negative pressure to a space between the dressing and the wound.

14. The kit of arrangements 13, further comprising a wound packing element positioned in the wound.

15. A method of visualizing a position of a tissue interface in a wound, comprising:
   positioning one or more visualization elements of any one of the previous arrangements in or on a first side of the wound, the visualization element or elements being configured to contrast with tissue in the wound;
   positioning one or more visualization elements of any one of the previous arrangements on a second side of the wound, the visualization element being configured to contrast with tissue in the wound; and
   monitoring a position of the visualization element or elements on the first side of the wound relative to a position of the visualization element or elements on the second side of the wound to determine the distance between the first and second sides of the wound.

16. A method of visualizing a position of a tissue interface in a wound, comprising:
   positioning a first visualization element in or on a first side of a wound interface, the visualization element being configured to contrast with a tissue in the wound;
   positioning a second visualization element in or on a second side of a wound interface, the visualization element being configured to contrast with a tissue in the wound; and
   monitoring a position of the first visualization element relative to a position of the second visualization element to determine the distance between the first and second sides of the wound.

17. The method of visualizing a position of a tissue interface in a wound of arrangement 16, wherein positioning a first visualization element in or on a first side of the wound interface comprises advancing a suture comprising a radiopaque material through at least a portion of the tissue on the first side of the wound.

18. The method of visualizing a position of a tissue interface in a wound of any one of arrangements 16-17, wherein positioning a first visualization element in or on a first side of the wound interface comprises advancing a suture comprising a radiopaque material through at least a portion of a peritoneum layer of tissue on the first side of the wound.

19. The method of visualizing a position of a tissue interface in a wound of any one of arrangements 16-18, wherein positioning a first visualization element in or on a first side of the wound interface comprises applying an adhesive comprising a radiopaque on at least a portion of a peritoneum layer of tissue on the first side of the wound.

20. The method of visualizing a position of a tissue interface in a wound of any one of arrangements 16-19, farther comprising removing the first visualization element and/or the second visualization element when the distance between the first side of the wound and the second side of the wound meets or exceeds a threshold distance.

21. A method of treating a wound, comprising:
   placing a wound packing member into the wound;
   applying a cover over the wound packing member and sealing the cover to skin surrounding the wound;
   applying negative pressure to the wound through the cover;
   monitoring the internal pressure in the wound; and
   controlling the closure of the wound by controlling the amount that the wound packing material collapses within the wound based on the monitored internal pressure, wherein the wound packing material collapse is controlled to ensure that the monitored internal pressure does not exceed a threshold value.

22. The method of treating a wound of arrangement 21, wherein the internal pressure is measured by monitoring at least one of a bladder pressure, an aortic pressure, a pressure within the colon, a pressure within the uterus, a limb pressure, and a blood flow rate.

23. The method of treating a wound of any one of arrangements 21-22, wherein the wound is an abdominal wound.

24. The method of treating a wound of any one of arrangements 21-22, wherein the wound is a wound on a limb.

25. The method of treating a wound of any one of arrangements 21-24, wherein the wound packing member comprises an adjustable volume wound filler.

26. The method of treating a wound of any one of arrangements 21-25, wherein the wound packing member comprises an inflatable sealed member and controlling the closure of the wound comprises controllably removing fluid or air from the inflatable member 27. The method of treating a wound of any one of arrangements 21-26, comprising detecting blood flow rate adjacent to the treated region using Laser Doppler velocimetry.

28. The method of treating a wound of any one of arrangements 21-27, further comprising positioning one or more wound visualization elements in a wound interface.

29. A method of treating a wound, comprising:
   placing a wound packing member into the wound;
   applying a cover over the wound packing member and sealing the cover to skin surrounding the wound;
   applying negative pressure to the wound through the cover; and controlling collapse of the wound packing member as the wound closes under negative pressure.

30. The method of treating a wound of arrangement 29, wherein the wound packing member is an inflatable bladder, and controlling collapse of the wound packing member comprises controlling the pressure within the bladder.

31. The method of treating a wound of any one of arrangements 29-30, comprising dynamically adjusting at least one of the volume, stiffness, pressure and collapse the wound packing member as the wound closes.

32. The method of treating a wound of arrangement 31, wherein the at least one of the volume, stiffness pressure and collapse of the wound packing member is dynamically adjusted based on internal pressure readings of the patient.

Other apparatuses, systems, methods and arrangements are also contemplated, which may or may not include some or all of the features described above. For example, wound treatment systems are contemplated that may utilize or perform one or more of the elements, kits or methods described above.

For example, in another embodiment, an apparatus for providing negative pressure wound therapy to a wound is provided. The apparatus may comprise a wound packing member or wound filler that has an adjustable volume, a backing layer for providing a substantially air and liquid-tight seal over a wound when the wound packing member or wound filler is positioned in the wound, and a source of negative pressure for providing negative pressure to a space beneath the backing layer. In some embodiments, a pressure sensor for measuring internal pressure is provided. Closure of the wound can be controlled by controlling the amount that the wound packing member or wound filler collapses based on the measured internal pressure.

In some embodiments, the pressure sensor for measuring internal pressure is configured to be placed in communication with a human organ. The wound packing member or wound filler may comprise a sealed member that can be controllably inflatable and deflatable from a pressure source. The apparatus may further comprise an organ protection layer configured to be positioned between the wound packing member or wound filler and the viscera or other organs. A further pressure sensor may be provided configured to monitor a pressure level within the sealed member. A pump may be configured to control a level of pressure within the sealed member. In further embodiments, a pressure sensor may also be provided for detecting pressure beneath the backing layer. A controller may be configured to adjust negative pressure based on one or more of the aforementioned pressure sensors.

In some embodiments, an apparatus may comprise at least three pressure sensors, the first pressure sensor configured to monitor a pressure level within the sealed member, the second pressure sensor being for detecting pressure beneath the backing layer, and the third pressure sensor being for measuring internal pressure within or on an organ. A controller may be configured to adjust one or more pressure levels under the backing layer and/or within the sealed member to reduced pressure exerted on the organ.

BRIEF DESCRIPTION OF THE DRAWINGS

Embodiments of the present disclosure will now be described hereinafter, by way of example only, with reference to the accompanying drawings in which:

FIGS. 1A and 1B illustrate embodiments of visualization elements.

FIG. 14 is a schematic representation of another embodiment of an apparatus used to provide negative pressure wound therapy to a wound, showing the wound in second state of contraction.

DETAILED DESCRIPTION OF THE PREFERRED EMBODIMENTS

Figure 1:
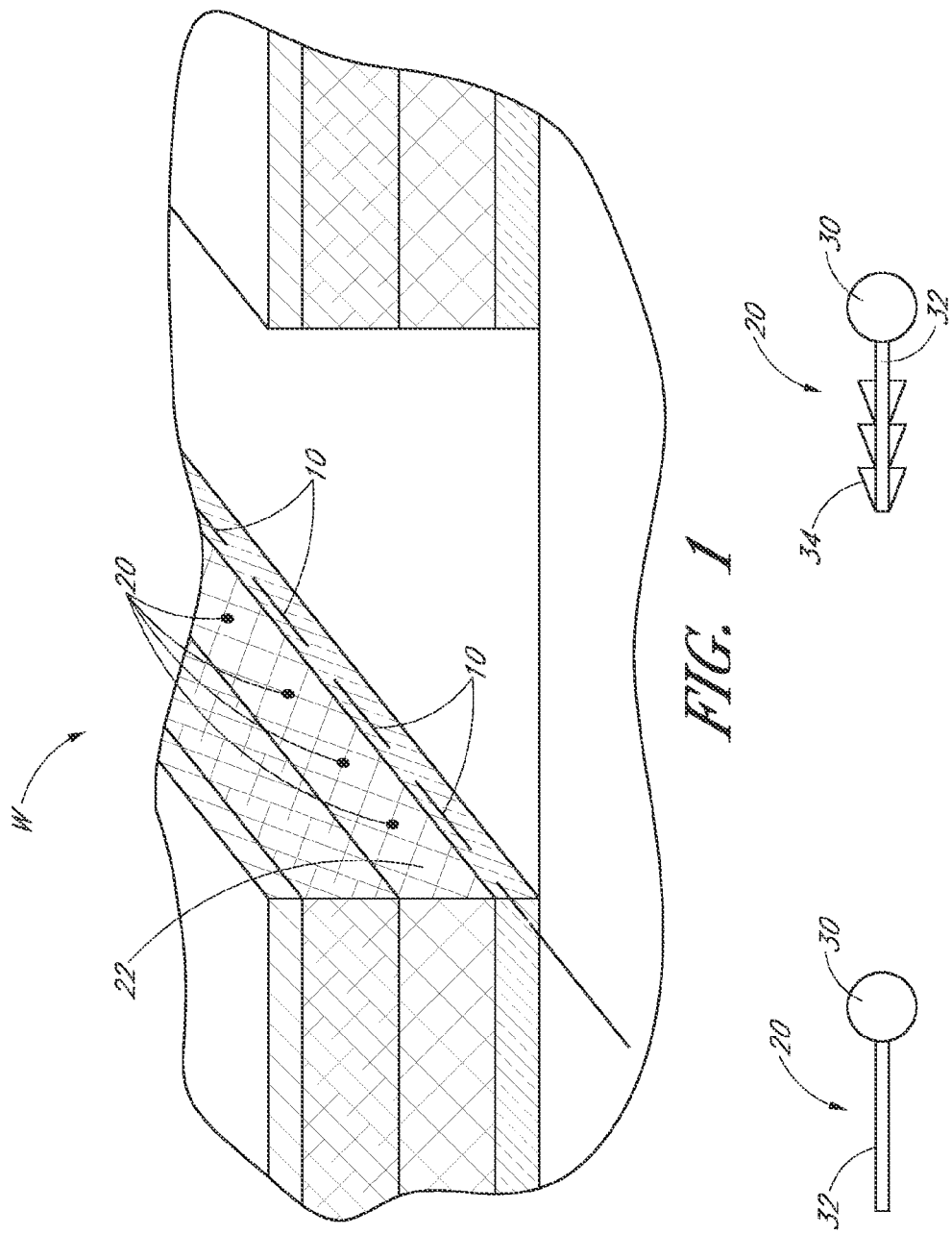
FIG. 1 is a schematic illustration of an embodiment of a wound interface visualization apparatus.

Some of the embodiments disclosed herein relate to apparatuses and methods of treating a wound with reduced pressure, including pump and wound dressing components and apparatuses. Generally, the embodiments including the wound fillers described herein may be used in combination with a negative pressure system comprising a drape or wound cover placed over the filler. A vacuum source, such as a pump, may be connected to the cover, for example, through one or more tubes connected to an aperture or port made in or under the cover. The apparatuses and components comprising the wound overlay and packing materials, if any, are sometimes collectively referred to herein as dressings. Further details of methods and apparatuses, such as dressing components and inflatable bladders, that are usable with the embodiments described herein are found in the following applications, which are hereby incorporated by reference in their entireties: U.S. Pat. No. 8,235,955, titled "Wound treatment apparatus and method," issued Aug. 7, 2012; U.S. Pat. No. 7,753,894, titled "Wound cleansing apparatus with stress," issued Jul. 13, 2010; Application Ser. No. 12/886,088, titled "Systems And Methods For Using Negative Pressure Wound Therapy To Manage Open Abdominal Wounds," filed Sep. 20, 2010, published as US 2011/0213287; application Ser. No. 13/092,042, titled "Wound Dressing And Method Of Use," filed Apr. 21, 2011, published as US 2011/0282309; and application Ser. No. 13/365,615, titled "Negative Pressure Wound Closure Device," filed Feb. 3, 2012, published as US 2012/0209227.

It will be appreciated that throughout this specification reference is made to a wound or wounds. It is to be understood that the term wound is to be broadly construed and encompasses open and closed wounds in which skin is torn, cut or punctured, or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. In some embodiments, the components of the negative pressure treatment system described herein can be particularly suited for incisional wounds that exude a small amount of wound exudate. Thus, while some embodiments and methods disclosed herein are described in the context of treating abdominal wounds, the apparatuses and methods disclosed herein are applicable to any wound in a body.

As is used herein, reduced or negative pressure levels, such as –X mmHg, represent pressure levels that are below standard atmospheric pressure, which corresponds to 760 mmHg (or 1 atm, 29.93 inHg, 101.325 kPa, 14.696 psi, etc.). Accordingly, a negative pressure value of –X mmHg reflects absolute pressure that is X mmHg below 760 mmHg or, in other words, an absolute pressure of (760–X) mmHg. In addition, negative pressure that is "less" or "smaller" than X mmHg corresponds to pressure that is closer to atmospheric pressure (e.g., –40 mmHg is less than –60 mmHg). Negative pressure that is "more" or "greater" than –X mmHg corresponds to pressure that is further from atmospheric pressure (e.g., –80 mmHg is more than –60 mmHg).

The negative pressure range for some embodiments of the present disclosure can be approximately –80 mmHg, or between about –20 mmHg and –200 mmHg. Note that these pressures are relative to normal ambient atmospheric pressure. Thus, –200 mmHg would be about 560 mmHg in practical terms. In some embodiments, the pressure range can be between about –40 mmHg and –150 mmHg. Alternatively a pressure range of up to –75 mmHg, up to –80 mmHg or over –80 mmHg can be used. Also in other embodiments a pressure range of below –75 mmHg can be used. Alternatively, a pressure range of over approximately –100 mmHg, or even 150 mmHg, can be supplied by the negative pressure apparatus. Unless stated otherwise, the term approximately is meant to represent a range of +/–10% of the stated value.

FIG. 1 is a schematic illustration of an embodiment of a wound interface visualization element. As illustrated in FIG. 1, in some embodiments and methods for the visualization of a surface of a wound interface, one or more first visualization elements 10 and/or second visualization elements 20 can be positioned along a surface of a wound W. The visualization elements can be positioned in fascia, peritoneum, fat, muscle, and/or any other tissue in the body.

In some embodiments, the first visualization elements 10 and/or second visualization elements 20 can comprise any suitable and biocompatible radiopaque material or a radiopaque marker for visualization during any suitable procedure, including, for example and without limitation, fluoroscopy, computerized tomography (CT) scan, x-ray, magnetic resonance imaging (MRI), or any other suitable visualization procedures or techniques applied during or after wound treatment, including without limitation negative pressure wound treatment. Any number or variety of radiopaque markers or visualization elements can be used.

The visualization element(s) can be sutures, a powder or solid material (such as a barium sulfate powder), or an adhesive comprising a radiopaque or contrasting material or element that can be applied at or adjacent to a surface of a wound. For example, in some arrangements, the visualization element(s) can be applied at or adjacent to an interface or wound surface of a fascia layer of tissue, the peritoneum, and/or any other suitable tissue layer.

As illustrated in FIG. 1, the visualization elements 10 can be radiopaque sutures (such as, without limitation, gold wire) applied in running or loopstitch along the length of a particular tissue layer in a wound interface. In the embodiment illustrated in FIG. 1, the tissue layer through which the visualization elements 10 are passed can be a fascia layer 12. However, any of the visualization element embodiments disclosed herein can be positioned in any desired tissue or tissue layer during surgery.

The sutures can comprise a radiopaque material. Additionally, though not required, the sutures can comprise a bioabsorbable material so that the sutures need not be removed from the wound after the target layer of tissue has progressed to a threshold or sufficient level of closure.

Additionally, in some embodiments, the visualization element can be an adhesive material, such as cyanoacrylate, or a powder comprising a radiopaque material such as barium sulfate, zirconium, gold, titanium, iodine, isohexol, iodixanol and tungsten oxide (any one or combination of which can be used with any other material or substance disclosed herein), can be applied to the surface of the subject layer of tissue to provide the contrast desired for visualization under fluoroscopy, computerized tomography (CT) scan, x-ray, magnetic resonance imaging (MRI), or during any other suitable visualization procedure or technique described herein or otherwise. The chosen materials for the visualization element should be biocompatible and also compatible with the chosen medical and visualization procedures and equipment.

Further, with reference to FIG. 1, any disclosed embodiments of the visualization elements, such as without limitation visualization elements 20, can be positioned in a fatty layer 22. In any embodiments, as illustrated in FIGS. 1A and 1B, the visualization elements can have a body portion 30 and a shaft portion 32. In some embodiments, the body portion can comprise one or more radiopaque studs, balls, or other radiopaque objects 30, which can be positioned on an end portion of a shaft portion 32. Additionally, in any embodiments, the visualization elements 20 can have one or more barbs or protrusions 34 extending in a transverse direction away from the shaft portion 32 for more secure engagement with the target tissue.

In the embodiment illustrated in FIG. 1, the tissue layer through which the visualization elements 20 are passed can be a fatty layer 22. However, any of the visualization element embodiments disclosed herein can be positioned in any desired tissue or tissue layer during surgery.

Any of the embodiments or details of the visualization elements described herein can be used with, or adapted for use with, negative pressure wound therapy dressings or components, surgical dressings or components used for closing wounds, or any other dressings or dressing components.

A number of experiments were conducted, using as the visualization element a gold wire used for jewellery making. The gold wire was very flexible, making it easy to position and pull though the tissue thus minimising trauma to the tissue. A further advantage of the being flexible is the fact that it does not impact on or hinder the contraction of the wound. Thus, in any embodiments disclosed herein, the visualization element can be flexible.

Other materials that may be suitable are titanium, tantalum, stainless steels, and corrosive resistant alloys, for example and without limitation Inconel, monel, hastelloy. Other materials that can be used include polymers filled with powdered radiopaque materials e.g. Barium Sulphate, titanium, zirconium oxide, iodine, iohexol, iodixanol. Additionally, the following non-resorbable polymers that can be used in conjunction with a contrast agent include, without limitation, nylon and polypropylene. Further improvements of some embodiments disclosed herein may be made by making the visualization elements from bioresorbable polymers. Suitable bioresorbable materials include polyglycolic acid, polylactic acid and caprolactan. Other suitable radiopaque materials may be so called radiopaque dyes e.g. low-osmolality contrast agents or less preferably high osmolality contrast agents. Use of bioresorbable polymers allows the visualization elements to be left within the tissue such that they will slowly dissolve over time without trace or substantially no trace.

Monofilaments of the above polymers may be produced by extrusion of the polymer premixed with a desired contrast agent. This will ensure the contrasting agent is spread uniformly throughout the visualization element and remain in contact with the substrate or other materials of the visualization element. Alternatively a master batch of the polymer containing the contrast agent may be made and then extruded or molded into the desired visualization element.

In further improvements, it may be desirable to utilize two or more visualization elements that include contrast agents of different contrast levels to show the movement of different layers of tissue in the body or different areas of the same tissue in the body. Closure of the fascial layer is one of the primary objectives of open abdominal treatments. So, monitoring the closure of the fascial layer is very important to ensuring a successful abdominal wound treatment. For example and without limitation, a metal may be used to give a contrast close to black whereas an inorganic salt (e.g., barium sulphate) may be used to give a contrast closer to white. Additionally, for example and without limitation, two or more visualization elements that define a different shape or which are similar in all regards but which are stitched in a different pattern can be used to show the movement of different layers of tissue in the body or different areas of the same tissue in the body. In this way the movement of different layers of tissue or different areas of the same tissue can be visualized and easily distinguished by a user in a 2-dimensional or other image.

Alternatively the contrasting agent maybe printed, sprayed, sputtered or coated onto the visualization element. In this way it may be possible to apply the contrasting agents at different spacings along the length or patterns on the visualization element thus allowing for differentiation of 2 or more different visualization elements in the body.

In the examples, the wire was looped through the fascia tissue in a running stitch format right around the wound such that the majority of the wire was not imbedded in the tissue, but ran along the surface of the tissue. This was achieved by threading the wire onto a standard curved surgical suture needle and passing through the tissue to create a running stitch.

The fluoroscope was positioned vertically over the centre of the wound. The contraction of the wound was watched in real time on the screen of the fluoroscope and still images were captured once movement had stopped. Using the fluoroscope in real time video mode, it is possible to see the tissue move and therefore visually determine the degree of closure being achieved in the deep tissue Other embodiments may include staples comprising a radiopaque material but minimising the number of parts used, which reduces the risk of any devices being left in the body after closure, unless the parts are bioresorbable. An alternative embodiment may include sprinkling radiopaque powder on the wound edge. In a further embodiment a radiopaque liquid or gel maybe painted or sprayed or spread on to the wound edge. Suitable liquids/gels may preferably be glues, advantageously their adherence to tissue prevents their movement after application. E.g. cyanoacrylate or fibrin glues filled with radiopaque powder. Such glues may also be used to help attach the main tissue closure device to the tissue.

In some embodiments, there can be a separate device attached to the tissue rather than the main closure device in case the main closure devices movement does not follow the movement of the tissue. Making the main closure device radiopaque also would help show differential movement.

Additionally, a surgeon or medical practitioner can place one or more visualization elements in a patient's dermis to detect a position of the dermis during the course of treatment. The one or more visualization elements in a patient's dermis can have a different level of contrast or a different shape as compared to the visualization elements that can be positioned in other layers of tissue. Or, the visualization elements can be positioned in the various tissue layers following a different pattern. For example, a radiopaque wire sutured through a first layer or fascial layer can have a first shape, a first pattern, and/or a first contrast level, and a radiopaque wire sutured through second layer or dermal layer can have a second shape, a second pattern, and/or a second contrast level. A first stitch pattern can have a wave-like stitch pattern having a first frequency and amplitude. A second stitch pattern can have a wave-like stitch pattern having a second frequency and amplitude so as to be discernible from the first stitch pattern.

Figure 2:
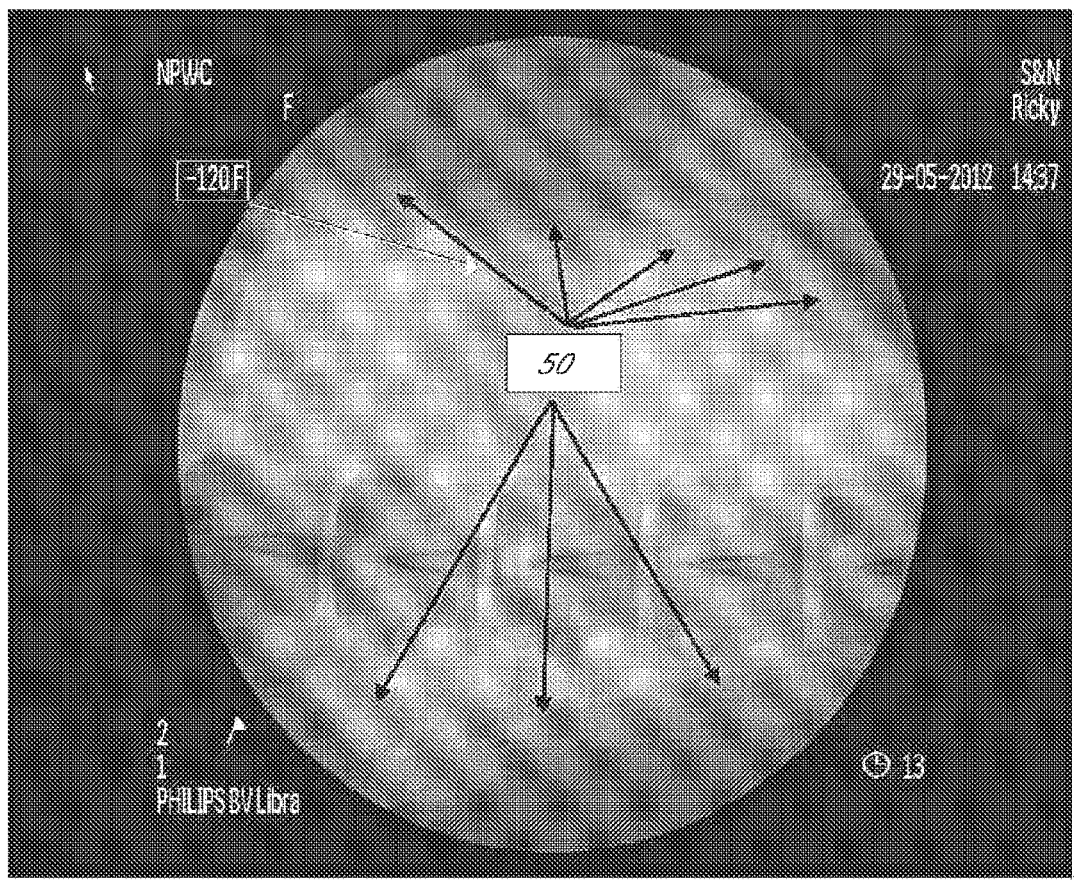
FIG. 2 is an image of an experimental setup of a wound having an embodiment or arrangement of a wound interface visualization apparatus, looking vertically down through the wound wherein no negative pressure has been applied to the wound.

A series of images were taken during experiments conducted having different embodiments of visualization element or arrangements, as shown in FIGS. 2-1i1, FIG. 2 is an image of an experimental setup of a wound having an embodiment or arrangement of a wound interface visualization element, looking vertically down through the wound wherein no negative pressure has been applied to the wound. The wound shown in FIG. 2 is packed with foam and covered with a drape. The visualization element 50 is a gold wire sewn through the fascia in a wave form pattern or path.

Figure 3:
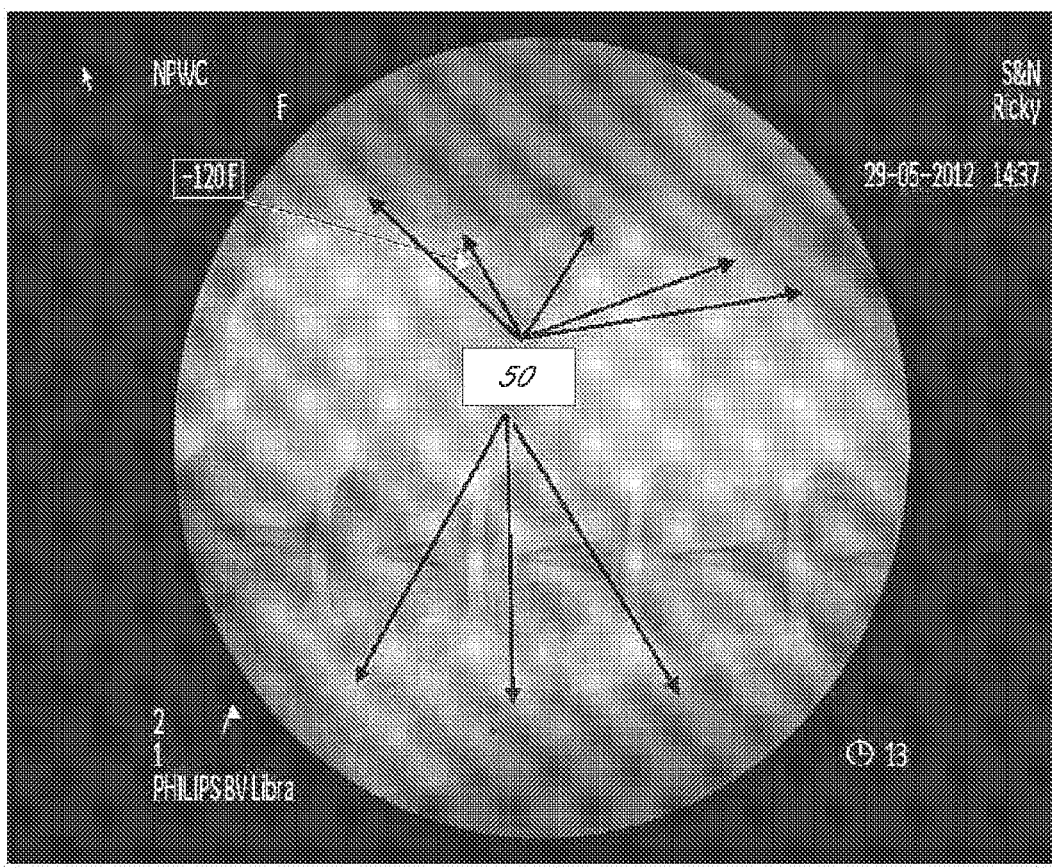
FIG. 3 is an image of the experimental setup of the wound having the embodiment or arrangement of a wound interface visualization element shown in FIG. 2, looking vertically down through the wound wherein negative pressure has been applied to the wound at a level of −120 mmHg.
Figure 4:
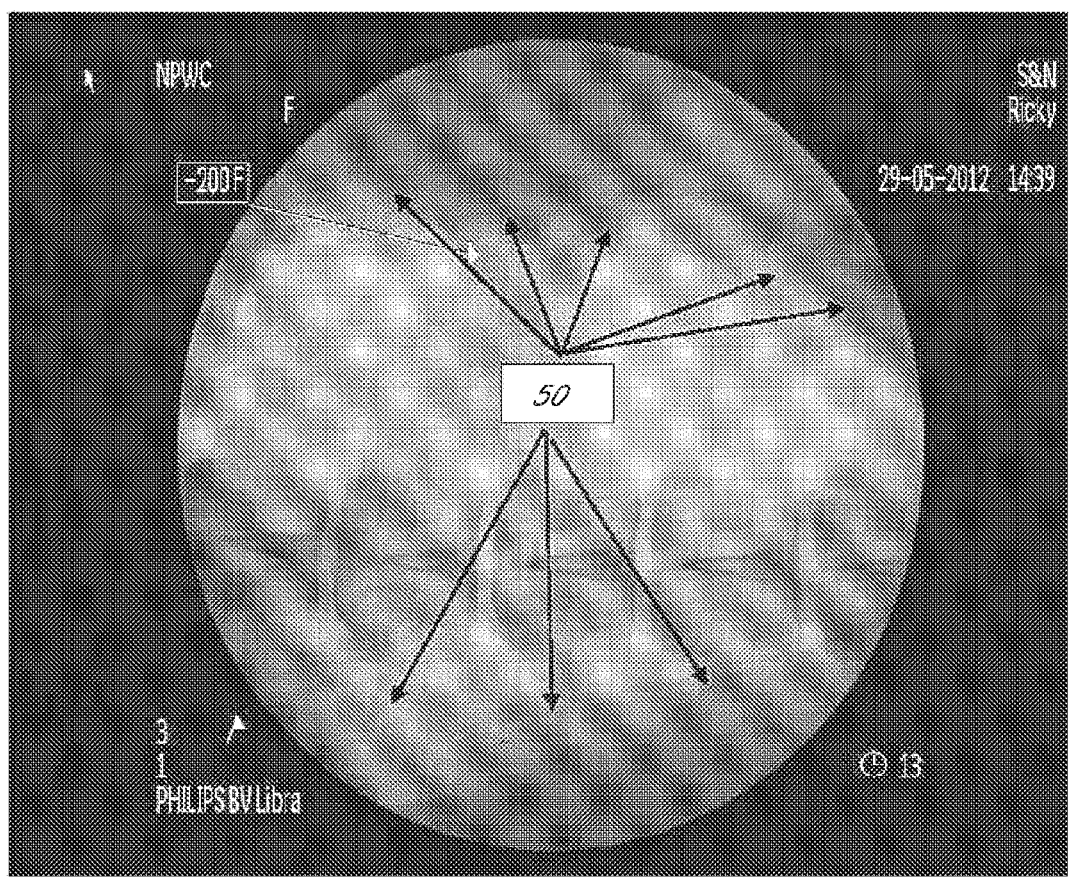
FIG. 4 is an image of an experimental setup of a wound having the embodiment or arrangement of the wound interface visualization element shown in FIG. 2, looking vertically down through the wound wherein negative pressure has been applied to the wound at a level of −200 mmHg.

FIG. 3 is an image of the experimental setup of the wound having the embodiment or arrangement of a wound interface visualization element shown in FIG. 2, looking vertically down through the wound wherein negative pressure has been applied to the wound at a level of −120 mmHg. In this experimental setup, as mentioned above, the wound is packed with foam and covered with a drape. Again, the visualization element 50 is a gold wire sewn through the fascia in a wave form pattern or path. In FIG. 3, a negative pressure of −120 mmHg. has been applied to the wound. The visualization element 50 provides a clear image and identification of the location of the interface of the facia layer to a surgeon or medical practitioner. FIG. 4 has the same experimental setup and visualization element embodiment as shown in FIG. 3, with a negative pressure level of −200 mmHg applied to the wound.

Figure 5:
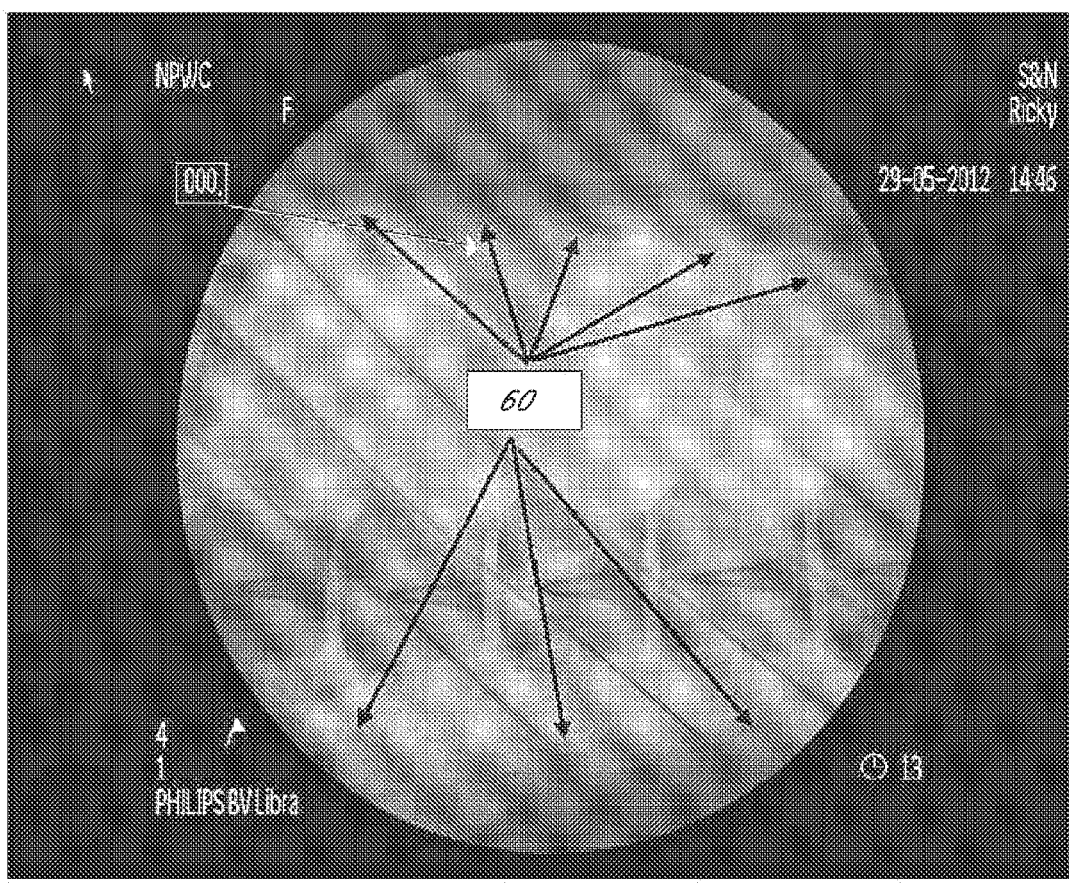
FIG. 5 is an image of an experimental setup of a wound having another embodiment or arrangement of a wound interface visualization element, looking vertically down through the wound wherein no negative pressure has been applied to the wound.
Figure 6:
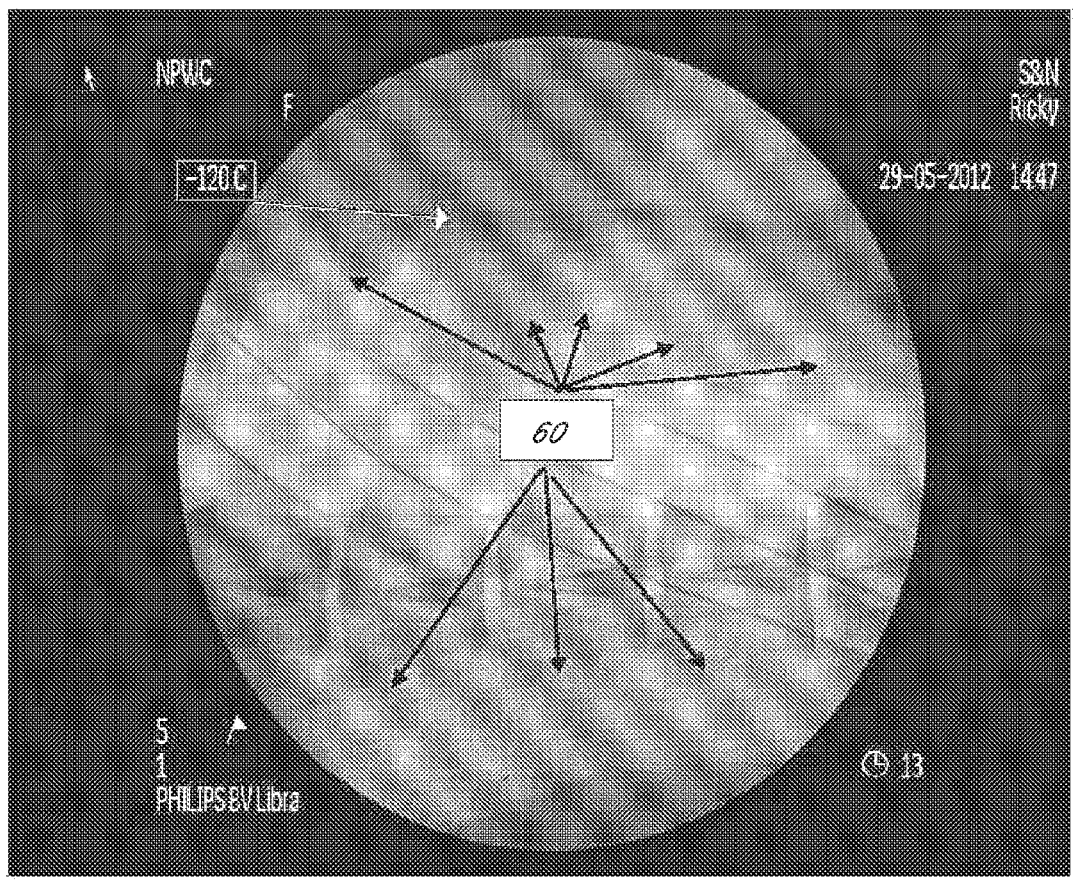
FIG. 6 is an image of an experimental setup of a wound having the embodiment or arrangement of a wound interface visualization element shown in FIG. 5, looking vertically down through the wound wherein negative pressure has been applied to the wound at a level of −120 mmHg.
Figure 7:
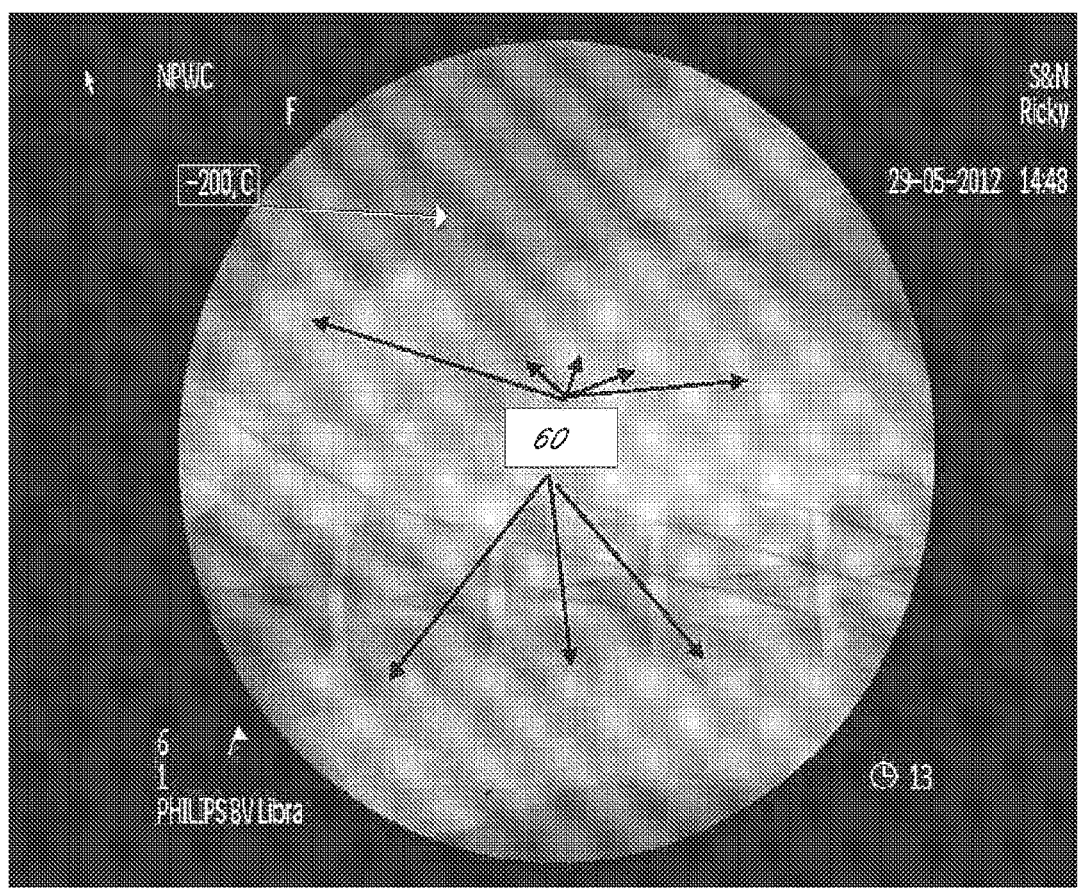
FIG. 7 is an image of an experimental setup of a wound having the embodiment or arrangement of a wound interface visualization element shown in FIG. 5, looking vertically down through the wound wherein negative pressure has been applied to the wound at a level of −200 mmHg.
Figure 8:
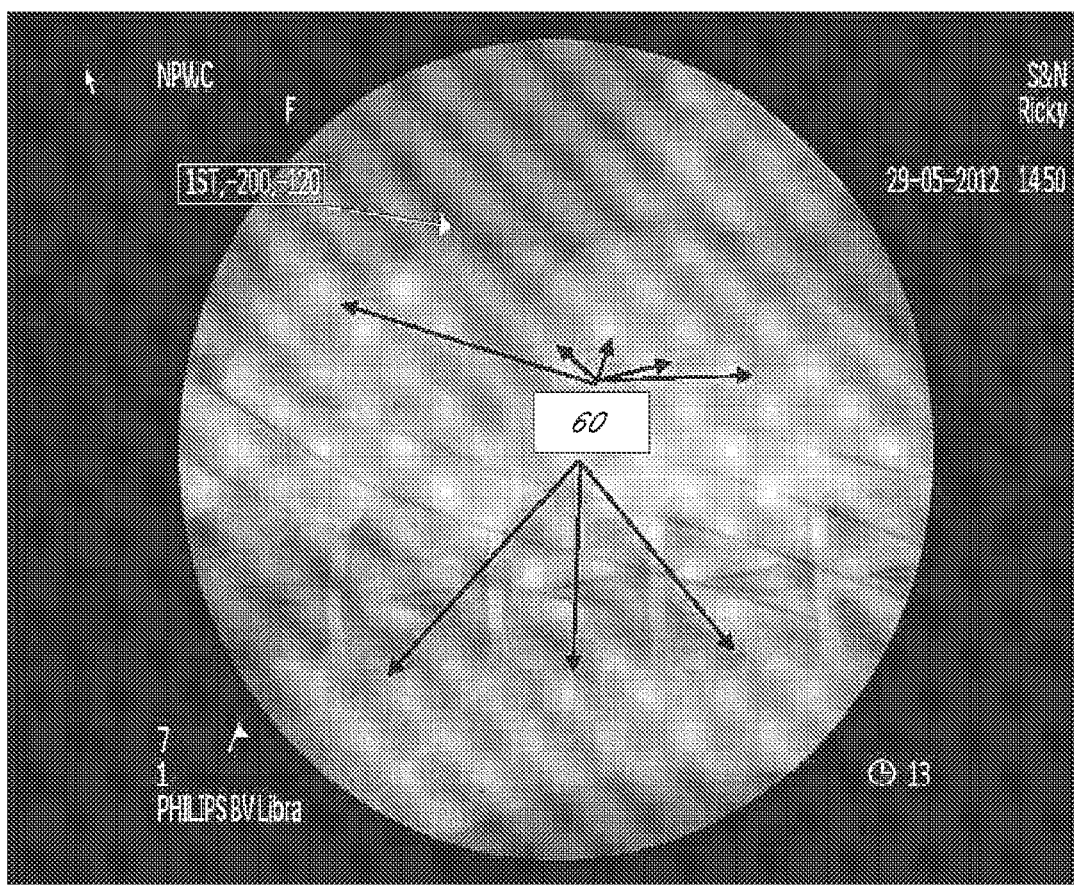
FIG. 8 is an image of an experimental setup of a wound having the embodiment or arrangement of a wound interface visualization element shown in FIG. 5, looking vertically down through the wound wherein negative pressure has been applied to the wound at a level of −200 mmHg, then released to −120 mmHg and held at −120 mmHg for the image.

FIGS. 5-7 are images of an experimental setup of a wound having another embodiment or arrangement of a wound interface visualization element 60, which again is a gold wire, sewn through the fascia in a wave form. In FIG. 5, the wound is subject only to atmospheric pressure. In FIG. 6, the level of negative pressure applied to the wound is −120 mmHg. In FIG. 7, the level of negative pressure applied to the wound is −200 mmHg. FIG. 8 is an image of the experimental setup of the wound having the embodiment or arrangement of the wound interface visualization element 60 shown in FIG. 5, looking vertically down through the wound wherein negative pressure has been applied to the wound at a level of −200 mmHg, then released to −120 mmHg and held at −120 mmHg for the image.

Figure 9:
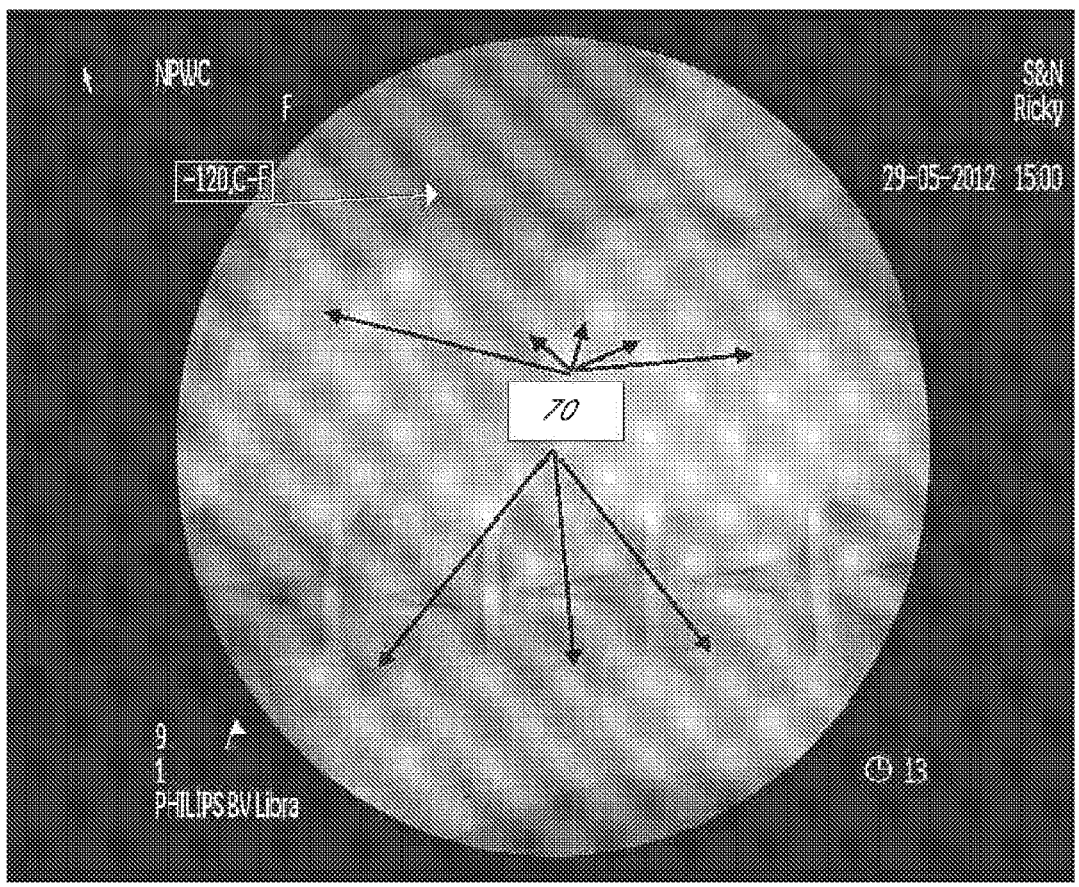
FIG. 9 is an image of an experimental setup of a wound having another embodiment or arrangement of a wound interface visualization element, looking vertically down through the wound wherein negative pressure has been applied to the wound at a level of −120 mmHg.
Figure 10:
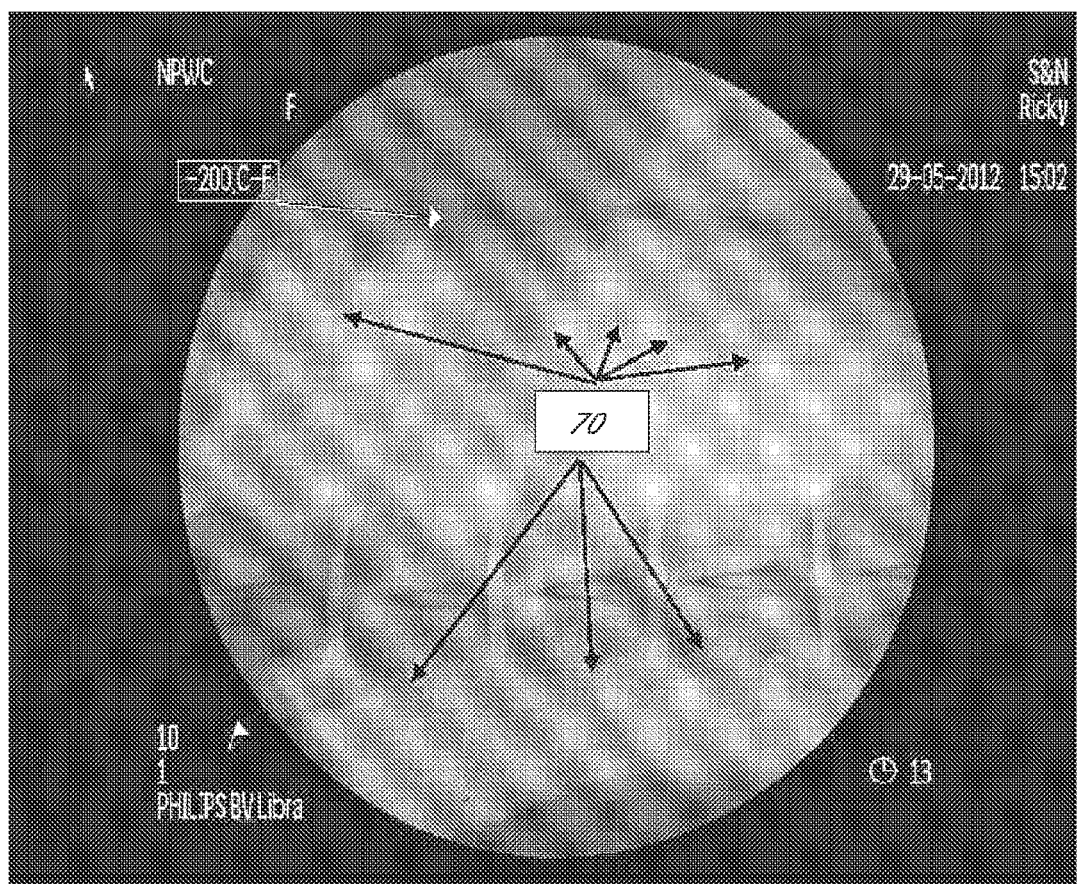
FIG. 10 is an image of an experimental setup of a wound having the embodiment or arrangement of a wound interface visualization element shown in FIG. 9, looking vertically down through the wound wherein negative pressure has been applied to the wound at a level of −200 mmHg.

FIG. 9 is an image of an experimental setup of a wound having another embodiment or arrangement of a wound interface visualization element 70, looking vertically down through the wound wherein negative pressure has been applied to the wound at a level of −120 mmHg. In this experimental setup, the wound has been packed with wound packing and foam inserts in cells and covered with drape. The visualization element 70, which was a gold wire in this experimental setup, is sewn through the fascia in a wave form. FIG. 10 is an image of the same experimental setup as shown in FIG. 9, showing the wound with negative pressure level of −200 mmHg applied to the wound.

Figure 11:
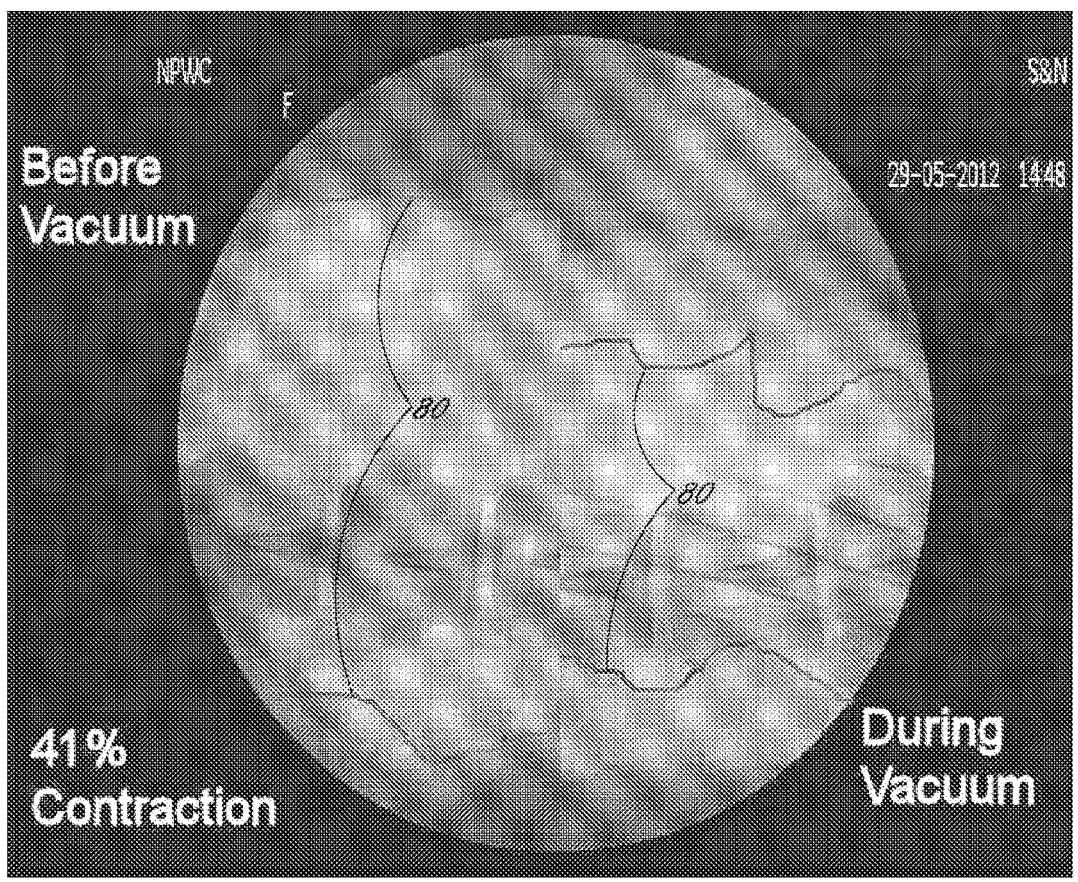
FIG. 11 is a split image showing, on the left hand side, an experimental setup of a wound having an embodiment or arrangement of a wound interface visualization element without application of negative pressure and looking vertically down through the wound, and on the right hand side, the same experimental setup of a wound shown in the left side, having the embodiment or arrangement of the wound interface visualization element shown in the left hand side of FIG. 11, having a vacuum applied to the wound at a level of −200 mmHg, and looking vertically down through the wound.

FIG. 11 is a split image showing, on the left hand side, an experimental setup of a wound having an embodiment or arrangement of a wound interface visualization element 80 without application of negative pressure and looking vertically down through the wound, and on the right hand side, the same experimental setup of a wound shown in the left side, having the embodiment or arrangement of the wound interface visualization element 80 shown in the left hand side of FIG. 11, having a vacuum applied to the wound at a level of −200 mmHg, and looking vertically down through the wound. Split image comparing the wound packing closure device at rest and after application of 200 mmHg of reduced pressure.

Compartment syndrome can occur when excessive pressure builds up inside an enclosed space in the body. Excessive pressures in the abdominal compartment, for example, can impede the flow of blood to and from the affected tissues, bodily organs, or even the lower extremities if excessive pressure is exerted on the abdominal aorta. The pressure buildup within the abdominal compartment can be the result of excessive fluid buildup in the abdominal compartment, in addition to or alternatively as a result of the forces exerted on the abdominal region from the application of negative pressure wound therapy to the abdominal compartment.

Such excessive pressure can cause permanent injury or damage to the tissues, organs (such as the liver, bowels, kidneys, and other organs), and other body parts affected by the reduction of blood flow. Therefore, preventing the buildup of excessive pressures in the abdominal compartment is beneficial for the treatment of abdominal injuries.

Internal abdominal pressure may also be measured and/or monitored indirectly using intragastric, intracolonic, intravesical (bladder), inferior vena cava catheters, or by other suitable methods, such as via the uterus. In some arrangements, for example, the internal pressure may be measured by inserting a catheter into the patient's bladder. Aortic blood pressure can also be monitored using techniques known in the field. For limb-based compartment syndrome, the internal pressure can be measured by a needle inserted into the affected limb, and preferably, the pressure measured there should be within 20-30 mmHg of the patient's diastolic blood pressure. The clinician can also monitor for a pulse distal of the affected extremity.

In addition to any of the foregoing methods or devices for measuring internal pressure, or any combination of such, in some embodiments, negative pressure wound therapy can be applied to the wound of a patient in a manner to minimize or prevent the build-up of excessive pressure that causes compartment syndrome. For example, any of the negative pressure wound therapy dressing components disclosed herein can be configured to support or contain one or more pressure sensors configured to permit a clinician to monitor the internal pressure within the compartment, wound cavity, or abdominal cavity. In some embodiments, the negative pressure dressing components may include a wound filler that may have an adjustable volume, such as an inflatable bladder or other wound fillers as described below, which when placed within a wound can control how much the wound can close. In one example, one or more pressure sensors can be added to the dressing components, including without limitation positioning one or more pressure sensors on the surface of and/or inside any inflatable bladder embodiment disclosed herein (such as described with respect to FIG. 12) that can be positioned in the abdominal cavity. The pressure sensors can be supported on, embedded within, or be integral with an outer and/or inner surface of any inflatable bladder embodiments disclosed herein, and can be used to monitor the pressure exerted on the inflatable bladder from the adjacent tissues and organs within the abdominal cavity to alert the patient or caregiver when a threshold or potentially harmful pressure is present within the abdominal cavity.

Additionally or alternatively, one or more pressure sensors can be positioned on or supported by a portion of any wound packing or wound filler components positioned within or adjacent to the wound cavity, or embedded within a portion of the wound filler and/or the dressing overlay or cover, including being supported by the overlay itself, and/or any conduit components of the dressing. The pressure sensors can therefore be positioned on, supported by, or embedded within any combination of the dressing components disclosed herein.

Furthermore, in addition or alternatively to any of the sensor positions located herein, one or more pressure sensors can also be positioned adjacent to one or more of the organs in the cavity being treated, for example the bladder, one or more kidneys, and/or any other organs or proximally located tissue surfaces.

Some embodiments can have one or more pressure sensors supported by or on or embedded within the wound packing layer or wound filler, one or more pressure sensors supported by or on or embedded within one or more of the organs (such as the bladder) or tissue layers in the cavity, and one or more pressure sensors supported by or on or embedded within one or more inflatable bladders positioned within the wound cavity.

Monitoring the pressure in one, some or all of these three locations can permit the caregiver to optimize or control the level of negative pressure applied to the wound cavity, optimize or control a level of inflation or pressure of an inflatable bladder placed within the wound, optimize or control the collapse, stiffness or volume of a wound filler placed within the wound, and/or monitor a level of pressure exerted on one or more organs, tissue layers, blood vessels, or other body parts affected by the closure pressures. A caregiver can then adjust a level of pressure in the inflatable bladder by either adding fluid to the bladder or releasing fluid from within the bladder to a receptacle or container positioned outside the body, adjust the collapse, stiffness or volume of the wound filler, adjust a level of negative pressure exerted on the wound cavity, and/or adjust any other closure forces applied to the wound to either increase or decrease the closure forces. In some embodiments, these adjustments can be made dynamically or automatically by a computer controller that receives one or more pressure readings or other data indicative of excessive pressure, and that sends a control signal to a pump or other device to make the adjustments.

A clinician may monitor the internal pressure as vacuum is slowly increased to the wound dressing, or as air is slowly released from the inflatable member. In one embodiment, human bladder pressure is controlled below approximately 40 mmHg, or below approximately 30 mmHg, approximately 20 mmHg, or approximately 15 mmHg. In some embodiments, the measurement of internal pressure and control of the vacuum and air release can be controlled automatically. This way as the oedema decreases the wound can be slowly closed further over, for example, a period of hours to days (e.g., closure by seven days). It will be appreciated that systems can be employed where the vacuum can be slowly applied with pressure feedback being provided based on vital signs of the patient or other monitoring described herein or in http://www.uptodate.com/contents/abdominal-compartment-syndrome.

Figure 12:
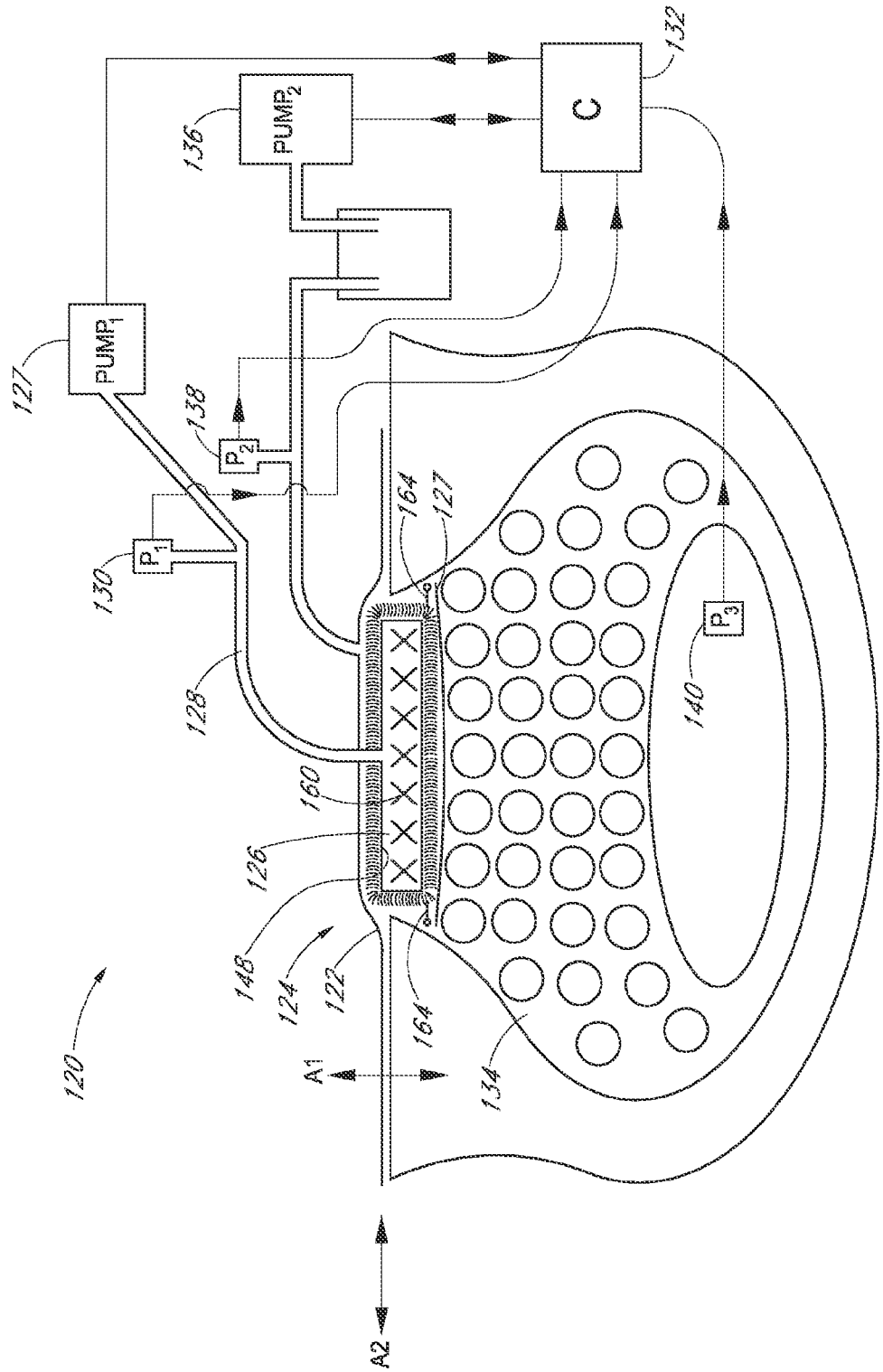
FIG. 12 is a schematic representation of an embodiment of an apparatus used to provide negative pressure wound therapy to a wound.

FIG. 12 is a schematic representation of an apparatus 120 used to provide negative pressure wound therapy to a wound and to control the level of therapy and/or closure of the wound based on pressure sensors positioned within the wound cavity to minimize the risk of compartment syndrome. For example and without limitation, in some embodiments, the apparatus 120 can have a backing layer 122 for providing a substantially air and liquid-tight seal over a wound. Under the overlay, the apparatus 120 can have a wound packing member or wound filler 124 that can have an adjustable volume and/or internal pressure. For example, some embodiments of the wound packing member 124 can have a sealed member 126 (such as a sealed bag) that can be controllably inflatable and deflatable from a pressure source such as a pump via a conduit 128 in communication with a sealed space within the sealed member 126. The sealed member 126 can be positioned in the wound in contact with the wound tissue interface. For example, in any embodiments used for abdominal wounds, the sealed member 126 can be configured and can be positioned in the wound cavity so as to engage all tissue layers above the organs in the body. For example, in some embodiments, the sealed member 126 can be positioned in the wound so as to contact any or all of the layers that can be present in an abdominal wound, such as (from deepest to most superficial) the peritoneum, extraperitoneal fascia (deep fascia), muscle, superficial fascia, subcutaneous tissue, and skin. However, the presence or absence of various layers is location dependent, so not all of these layers may be present in every abdominal wound treatable with the apparatuses of the present disclosure.

In some embodiments, an organ protection layer 127, such as any embodiments of the wound contact layer disclosed in U.S. Application Publication No. 2011/0213287, Ser. No. 12/886,088, titled SYSTEMS AND METHODS FOR USING NEGATIVE PRESSURE WOUND THERAPY TO MANAGE OPEN ABDOMINAL WOUNDS, filed on Sep. 20, 2010, which application is hereby incorporated by reference herein as if fully set forth herein, can be positioned between the sealed member 126 and the viscera or other organs. Embodiments of the apparatus 120 disclosed herein can comprise any of the other components, materials, features, or details of any of the embodiments or components of the negative pressure systems disclosed in U.S. application Ser. No. 12/886,088. As mentioned, all embodiments or components of the negative pressure systems disclosed in U.S. application Ser. No. 12/886,088 are hereby incorporated by reference as if fully set forth herein.

A pressure sensor 130 (also referred to herein as a first pressure sensor) can be used to monitor a pressure level within the sealed member 126. The pressure sensor 130 can provide a visual reading of the level of pressure within the sealed member 126, and/or can provide a signal to a controller 132 based on the level of pressure within the sealed member.

The level of pressure within the sealed member 126, as mentioned, can be controlled in part by the pump 127 (also referred to herein as the first pump) and can be adjusted to be a positive or a negative pressure. Additionally, in some embodiments, the pump 127 can be configured to cycle the pressure level between any desired positive or negative pressure levels or to apply intermittent pressure to the sealed member 126. Positive pressures within some embodiments of the sealed member 126 or any sealed member embodiment disclosed herein can range from 0 mmHg to 60 mmHg or more. Negative pressures within some embodiments of the sealed member 126 or any sealed member embodiment disclosed herein can range from 0 mmHg to −180 mmHg or more.

In any embodiments disclosed herein, the pressure level within the sealed member 126 can be controlled independently of the pressure in a space 134 beneath the backing layer 122. The pressure beneath the backing layer 122 can be detected by a pressure sensor (such as pressure sensor 138, which is also referred to herein as a second pressure sensor) in communication with the space 134 beneath the backing layer 122. The second pressure sensor 138 can be configured to provide a signal to the controller 132. In any embodiments disclosed herein, a second pump, such as pump 136, can be used to provide a source of negative pressure to a space 134 beneath the backing layer 122. Alternatively, the apparatus can be configured to have only one pump (not illustrated) having multiple conduits and multiple valves to independently control a level of pressure within the sealed member 126 and the space 134 beneath the backing layer 122.

In some embodiments, the level of pressure within the sealed member 126 can be adjusted independent of the level of reduced pressure in the space 134 to increase or decrease a volume of the sealed member 126, which can be beneficial in terms of controlling a level of pressure exerted on one or more organs in the abdominal area and, hence, can be beneficial in terms of controlling or minimizing a risk of compartment syndrome. A pressure sensor 140 (which is also referred to herein as a third pressure sensor) can be placed in communication with a human organ, for example the human bladder to monitor pressure within the human bladder. The third pressure sensor 140 can also be configured to provide a signal to the controller based on the pressure reading detected by the third pressure sensor 140.

If a pressure detected in one or more organs, such as the human bladder, as detected by a pressure sensor 140, exceeds a threshold value, the controller 132 can adjust one or more pressure levels to reduce the pressure exerted on the organ or organs. In some embodiments, the threshold value of pressure measurements for organs in the abdominal region can be 10 mmHg (or approximately 10 mmHg), or 12 mmHg (or about approximately 12 mmHg), or 15 mmHg (or about 15 mmHg) but such values may be organ specific and/or patient specific. Additionally, in some applications, wherein any of the dressings disclosed herein are used to treat a wound on the thigh, for example, compartment pressures can reach as high as 120 mmHg, such that the threshold value of compartment pressure in that region may be much higher than for abdominal wounds, such as approximately 60 mmHg or less to approximately 80 mmHg, or approximately 100 mmHg. In the leg, generally, the threshold value of pressure which can trigger such pressure and dressing adjustments can be approximately 40 mmHg, or from approximately 40 mmHg to approximately 60 mmHg. Some embodiments of the apparatus can configured such that a medical practitioner can set the level of the threshold value, since a different value may be applicable to each patient. For younger patients or children, or patients that are at a higher risk for developing compartment syndrome, for example, a lower threshold value can be set. In some embodiments, the threshold value can be set at from approximately 8 mmHg to approximately 12 mmHg.

For example, in abdominal negative pressure wound therapy kits, to reduce the pressure buildup, the apparatus can be configured to decrease the level of closure forces applied to the wound. This can be achieved in some embodiments by increasing a level of pressure in the sealed member 126, thereby limiting the amount of closure in the walls of the wound interface even when an elevated level of reduced pressure applied to the space 134 in the wound is maintained to ensure an appropriate level of fluid removal. This can be done until the level of pressure in one or more of the organs, such as the bladder, or blood flow rate measurements, reach a safe or below-threshold value once again. In some embodiments, the pressure level within the sealed member 126 can be a positive value (i.e., above atmospheric) to exert a spreading force on the tissue interface, while the pressure level within the space 134 but outside of the sealed member 126 is at a negative pressure level. This arrangement wherein the sealed member 126 can independently control the level of closure of the wound interface, can also permit a medical practitioner to exceed the normal negative pressure levels in the space 134 beyond the typical therapeutic ranges that might otherwise have been limited by excessive interabdominal pressure levels.

In some embodiments or arrangements, a sealed member 126 can be sized and configured to contact the peritoneum, extraperitoneal fascia (deep fascia), muscle, superficial fascia, subcutaneous tissue, and skin when placed in the abdominal wound. When the level of closure of the wound interface is desired to be limited, such as when excessive levels of pressure are present in or adjacent to the wound area, a level of pressure within the sealed member 126 can be increased to limit the contraction in one or more of the peritoneum, extraperitoneal fascia (deep fascia), muscle, superficial fascia, subcutaneous tissue, and skin, thereby increasing the volume of space that the viscera can occupy and reducing the level of pressure exerted on the various organs and blood vessels. Again, because the level of pressure within the sealed member 126 can be adjusted independently of the level of pressure within the space 134 beneath the backing layer 122 but outside of the sealed member 126, a therapeutic level of reduced pressure can be applied to the wound to remove excessive liquid exuded in the abdominal compartment and improve the healing conditions.

In any of embodiments disclosed herein, the apparatus can gather pressure readings from one or more pressure sensors positioned throughout the body to monitor compartment pressures. For interabdominal compartment pressures, readings can be gathered in the abdominal region or adjacent thereto. For example, any apparatus disclosed herein can have one or more blood flow meters (such as a laser Doppler blood flow meter) configured to measure a flow rate of blood through target blood vessels, arteries, capillaries, and/or muscles. Any embodiments of the laser Doppler can be permanently mounted to the patient's skin near the wound cavity. In some embodiments, for example, one or more blood flow meters can be used to measure a flow rate of blood through the femoral arteries or through musculature at or near to the abdominal region and provide a feedback signal to the controller 132.

Additionally, in some embodiments, pressure levels in, for example, the abdominal compartment can be measured using the vesicular technique, which can involve the use of an indwelling urinary catheter, a pressure transducer, and a syringe or similar device capable of infusing fluid. Additionally, pressure levels in the abdominal compartment can be measured by catheterizing the inferior vena cava through either the left or right femoral artery. See F. Luti, A. Sangosanya, and L. J. Kaplan, "Abdominal Compartment Syndrome: Clinical Aspects and Monitoring," *Critical Care Clinics*, vol. 23, no. 3, pp. 415-433, 2007 for more information about monitoring techniques for suitable for monitoring abdominal compartment syndrome.

Further, any embodiments of the sealed member 126 disclosed herein can be formed from a substantially sealed impermeable membrane 148, that seals around or to the conduit 128 that provides the fluid (e.g., air, nitrogen, or argon, or saline, water, or other liquids) into and out of the impermeable membrane 148, which can be formed from any suitable, biocompatible polymer film, sheet, bag, pouch, chamber, or otherwise, similar to any of the inflatable membranes disclosed in U.S. Pat. No. 7,753,894, which is application Ser. No. 12/886,088, titled WOUND CLEANSING APPARATUS WITH STRESS, filed on Dec. 17, 2007.

In some embodiments, the sealed member 126 can have a foam layer 150 around some or all of the outside surface of the impermeable membrane 148, in some embodiments, the foam layer 150 can surround the entire surface of the impermeable membrane 148. The foam 150 can help cushion any pressure points exerted on the tissue by the sealed member 126, and can assist with the distribution of negative pressure across the wound cavity.

Additionally, though not required, any embodiments disclosed herein can have a structural member 160 positioned inside the impermeable membrane 148. In some embodiments, the structural member 160 can be configured to be more rigid in a vertical direction (i.e., transverse to the backing layer, as indicated by arrow A1 in FIG. 12), than in a lateral direction (i.e., in the direction of wound closure of the tissue interfaces, as indicated by arrow A2 in FIG. 12). Examples of structural members that can be used are found in application Ser. No. 13/365,615, titled "Negative Pressure Wound Closure Device," filed Feb. 3, 2012, published as US 2012/0209227, the entirety of which is hereby incorporated by reference.

In some embodiments, the sealed member 126 can have multiple, independently controllable (e.g., inflatable or deflatable) chambers. One or more manifolds can control the inflation and deflation of the various compartments or chambers to control the size and/or shape of the bladder member as desired to suit the particular wound size and application.

Additionally, in any embodiments disclosed herein, the sealed member 126 can be used with a vertically rigid but laterally collapsible structure positioned either inside or outside of the sealed member 126. For example, with reference to FIG. 13, another embodiment of an apparatus 200 is illustrated. The apparatus 200 can have any of the same features, components, or details of any other embodiments disclosed herein, including any of the visualization elements and the pressure sensors disclosed above. Additionally, as shown in FIG. 13, a sealed member 206 can be positioned in the wound cavity and have any of the same features, materials, or other details of the sealed member 126 disclosed herein, including but not limited to the foam layer or interface 208 surrounding the impermeable layer 210.

The apparatus 200 can also have a support member 216 positioned under a backing layer 218. Some embodiments of the support member 216 can have one or more legs (also referred to herein as a body portion) 220 attached to a top portion 226 (also referred to herein as a first portion) of the support member 216. In some embodiments, the top portion 226 of the support member 216 can be along an apex of the support member 216 and define a longitudinal axis A1 of the support structure. The legs 220 can be rotatably supported by the top portion 226 so that the legs 220 can rotate about axis A1 defined through the axial centerline of the top portion 226. The sealed member 206 can be coupled with, connected to, adhered to, or otherwise attached the legs 220 such that contracting or expanding the sealed member 206 will correspondingly contract or expand the legs 22 and support member 216, in some embodiments, the legs 220 can be positioned within molded pockets formed in the sealed member 206, in some embodiments, one or more foam pockets positioned at the bottom of the legs 220 can be adhered to the sealed member 206.

Figure 13:
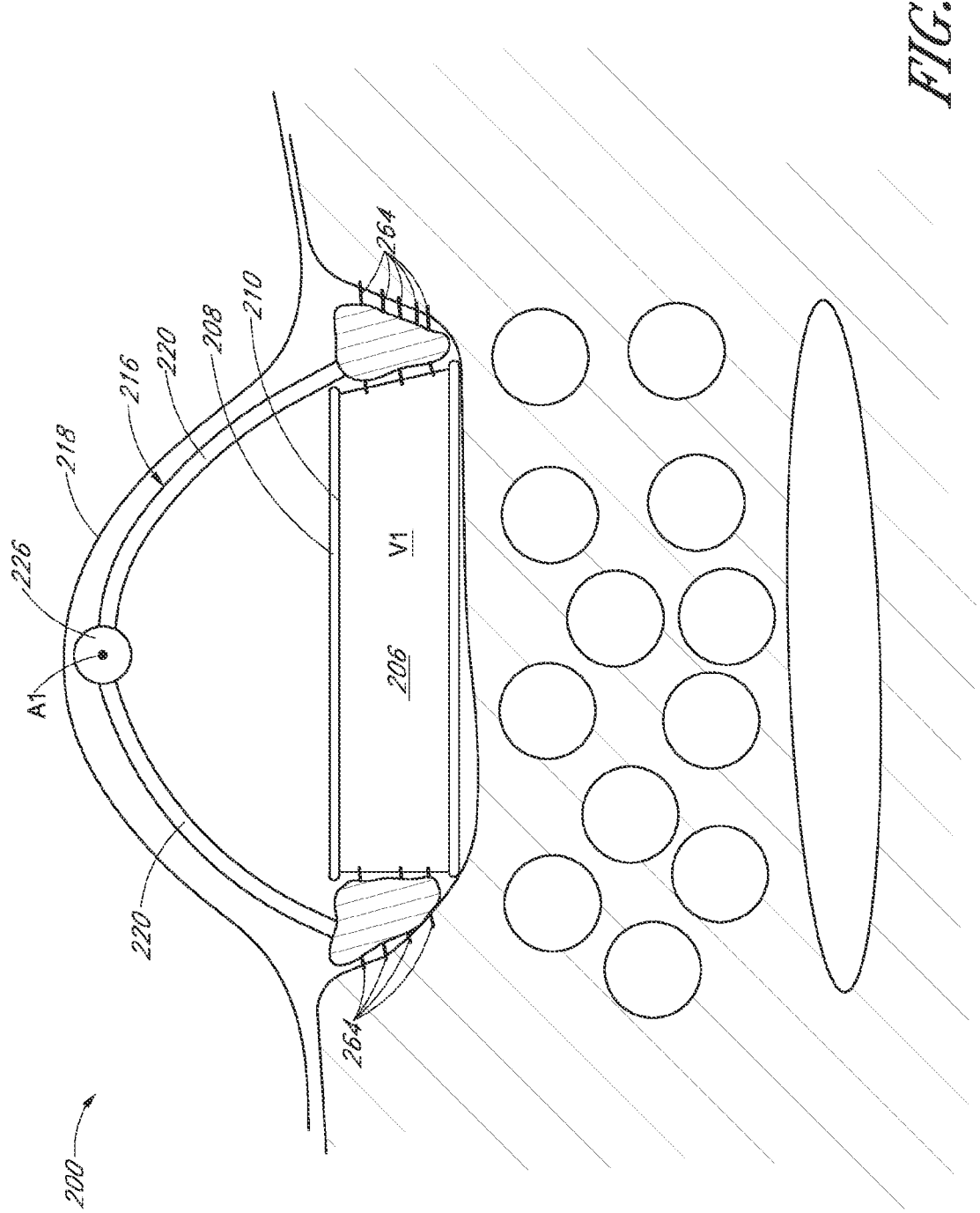
FIG. 13 is a schematic representation of another embodiment of an apparatus used to provide negative pressure wound therapy to a wound, showing the wound in first state of contraction.

In this configuration, as the sealed member 206 is contracted from a first volume, such as volume V1 shown in FIG. 13, to a second, larger volume, such as volume V2 shown in FIG. 14, the support member 216 (or any other suitable support member having greater vertical than lateral rigidity) can also laterally contract. Additionally, the sealed member 206 can be configured to expand from a smaller volume, such as volume V2 shown in FIG. 14, to a larger volume, such as volume V1 shown in FIG. 13, the so as to urge the support member 216 and the legs 220 thereof, laterally outward against the walls of the wound interface, thereby potentially reducing the pressure on the organs within the abdominal compartment. As the wound closes during the course of healing, the legs 220 can rotate closer together so that the closure of the wound is not inhibited by the dressing backing layer 218.

Further, some embodiments of the wound closure apparatuses, such as embodiments 120 and 200, can have one or more tissue engaging elements supported by the sealed member or the support member in communication with the sealed member. The tissue engaging elements can be configured to engage one or more layers of the wound interface, including any one or combination of the peritoneum, extraperitoneal fascia (deep fascia), muscle, superficial fascia, subcutaneous tissue, and skin. The tissue engaging elements 164 (schematically represented in FIG. 12) of the embodiment of the apparatus 120 shown in FIG. 12, or the tissue engaging elements 264 of the embodiment of the apparatus 200 can comprise any one or combination of tissue connectors, tissue anchors, hook shaped members, balls on the ends of rods, and/or any other suitable engaging mechanisms available for use with the various layers of tissue. Some embodiments of the sealed member 126 can have any combination of different tissue engaging elements desired to engage the various different tissue layers in the wound site.

In any embodiments of the sealed member disclosed herein, a level of the volume of fluid within the sealed member can be controlled automatically by the control system, as discussed. Additionally, in any embodiments, the level of the volume of fluid within the sealed member can be changed manually by adding or removing fluid into the sealed member through a tube and a hand operated pump system, or through a syringe and cannula device inserted into a sealed receptacle such as one or more syringe ports on the sealed member, in response to pressure readings acquired by any of the plurality of pressure sensors in the apparatus.

In some embodiments, the sealed member can itself be more rigid in a vertical direction than in a lateral direction. For example, any embodiments of the sealed member can have corrugations or an undulating surface that causes the sealed member to be more flexible in a lateral direction than in a vertical direction. In some embodiments, the sealed member can have, for example, an accordion-like shape.

It will be appreciated that in some embodiments, it is not necessary to take any measurements indicative of excessive pressure within the patient. Rather, it may simply be desired to control the closure of a wound by controlling the volume, stiffness, pressure, and/or collapse of any of the wound fillers described above. Such closure can be controlled based on visual inspection, use of the wound visualization methods and apparatus described above, or can be controlled based on a desired predetermined schedule. The control over such closure can be performed manually by a health practitioner, or may be performed automatically or based on inputs by a controller as described above. For example, where an inflatable bladder is placed in the wound, the pressure in the bladder may be manually or automatically controlled to limit and/or allow a certain amount of wound closure for a given period of time. This concept may similarly be applied to wound fillers such as described in FIG. 13 by including a mechanism (such as the adjustable bladder between the legs) where the angle between the legs can be controlled over time.

Other embodiments of wound fillers whose volume, stiffness, pressure and/or collapse may be controlled, can be used with any of the components of any of the embodiments disclosed herein. Examples of such additional wound fillers that can be used with any of the components of any of the embodiments disclosed herein are found in application Ser. No. 13/365,615, titled "Negative Pressure Wound Closure Device," filed Feb. 3, 2012, published as US 2012/0209227, incorporated by reference herein, the entirety of which is hereby incorporated by reference. FIGS. 15A-F illustrate further embodiments of suitable wound fillers, and examples of these and other suitable wound fillers may be found in U.S. Pat. No. 7,754,937, titled "WOUND PACKING MATERIAL FOR USE WITH SUCTION," the entirety of which is hereby incorporated by reference. Other embodiments of negative pressure therapy apparatuses, dressings, wound fillers and methods of using the same that may also be utilized alone or in combination with the embodiments described herein, and further description of the embodiments found above, for example with respect to FIGS. 13 and 14 above, are found in U.S. Provisional Application No. 61/681,037, filed Aug. 8, 2012, entitled WOUND CLOSURE DEVICE, and PCT Application No. PCT/US13/42064 filed May 21, 2013, entitled WOUND CLOSURE DEVICE, the entireties of which are hereby incorporated by reference. It will be appreciated that any of these embodiments of wound fillers may also be used in combination with or instead of the inflatable bladder in the system and method of FIG. 12.

Figure 15A:
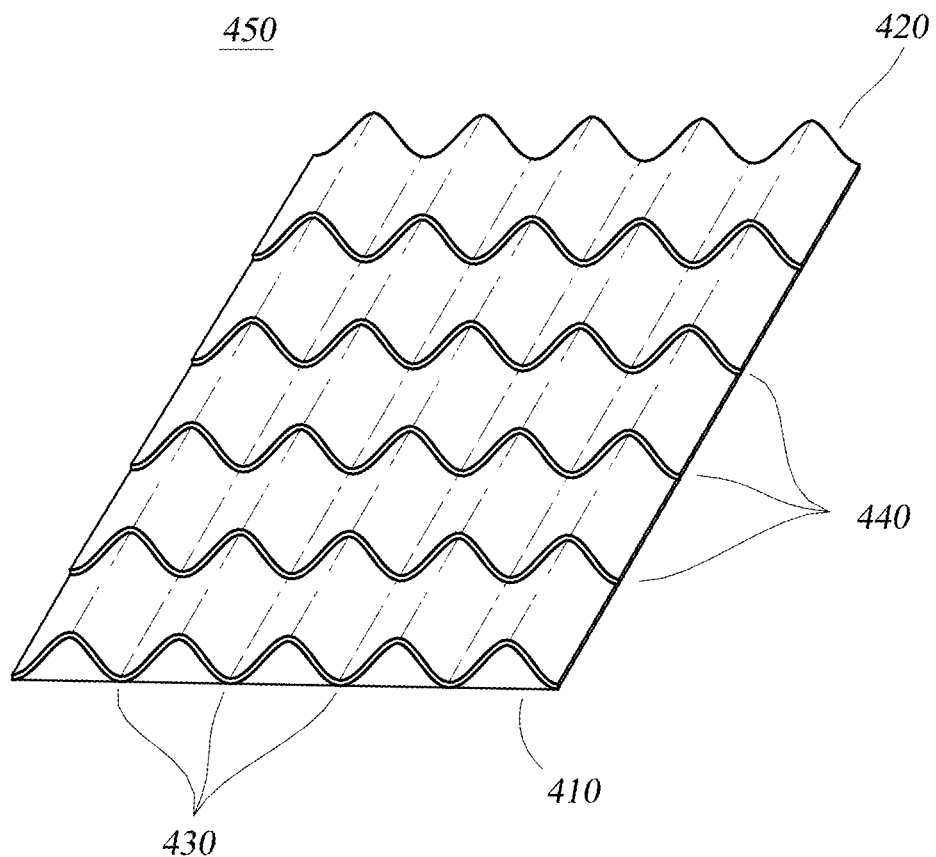
FIGS. 15A-15F illustrate further embodiments of wound fillers.

FIG. 15A illustrates a wound filler comprising a corrugated unit 450 comprising two sheets. A first sheet layer 410 is provided, and a second sheet-like layer 420 having an essentially sinusoidal cross section, for example, is coupled to the surface of the first sheet layer at locations 430. The coupling can be achieved by use of an adhesive or heat sealing. A two part silicone adhesive has been found suitable to provide coupling between sheet 410 and sheet 420. A bead of silicone material 440 may be optionally added to adjust the resiliency of the corrugated unit 450. A suitable sheet material is polyester or polyester fibers. Although sheet layer 420 is illustrated as having a sinusoidal cross-section, it is also contemplated that other cross-sections, such as pleated, may be used.

Figure 15B:
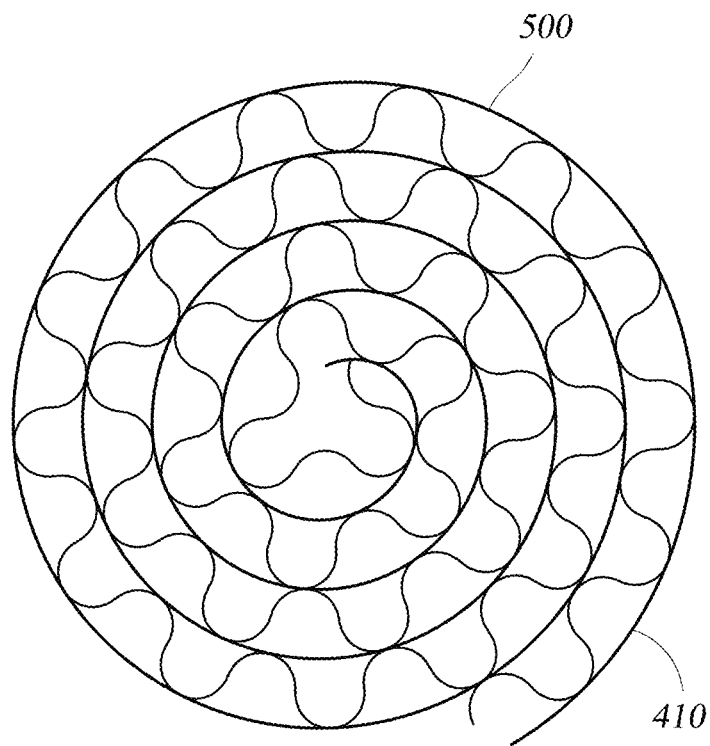
Figure 15C:
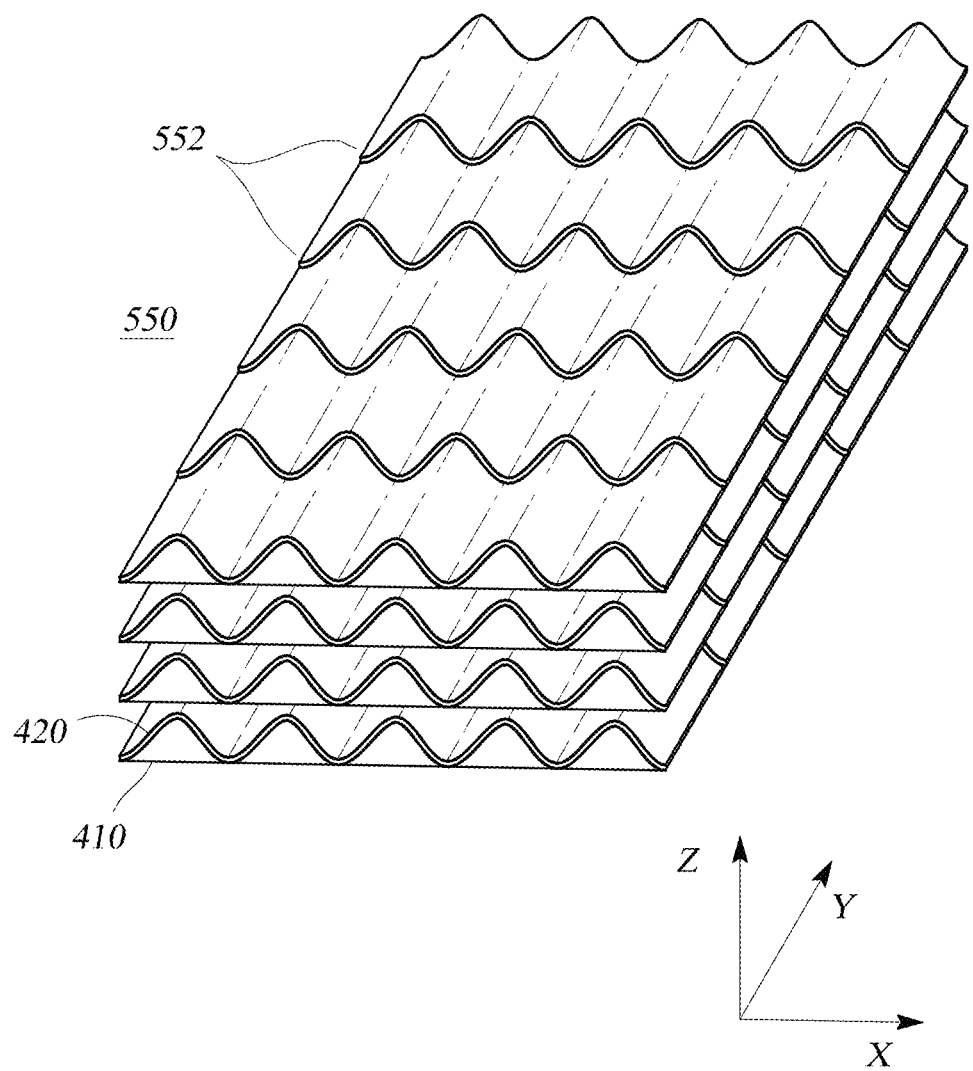
Figure 15D:
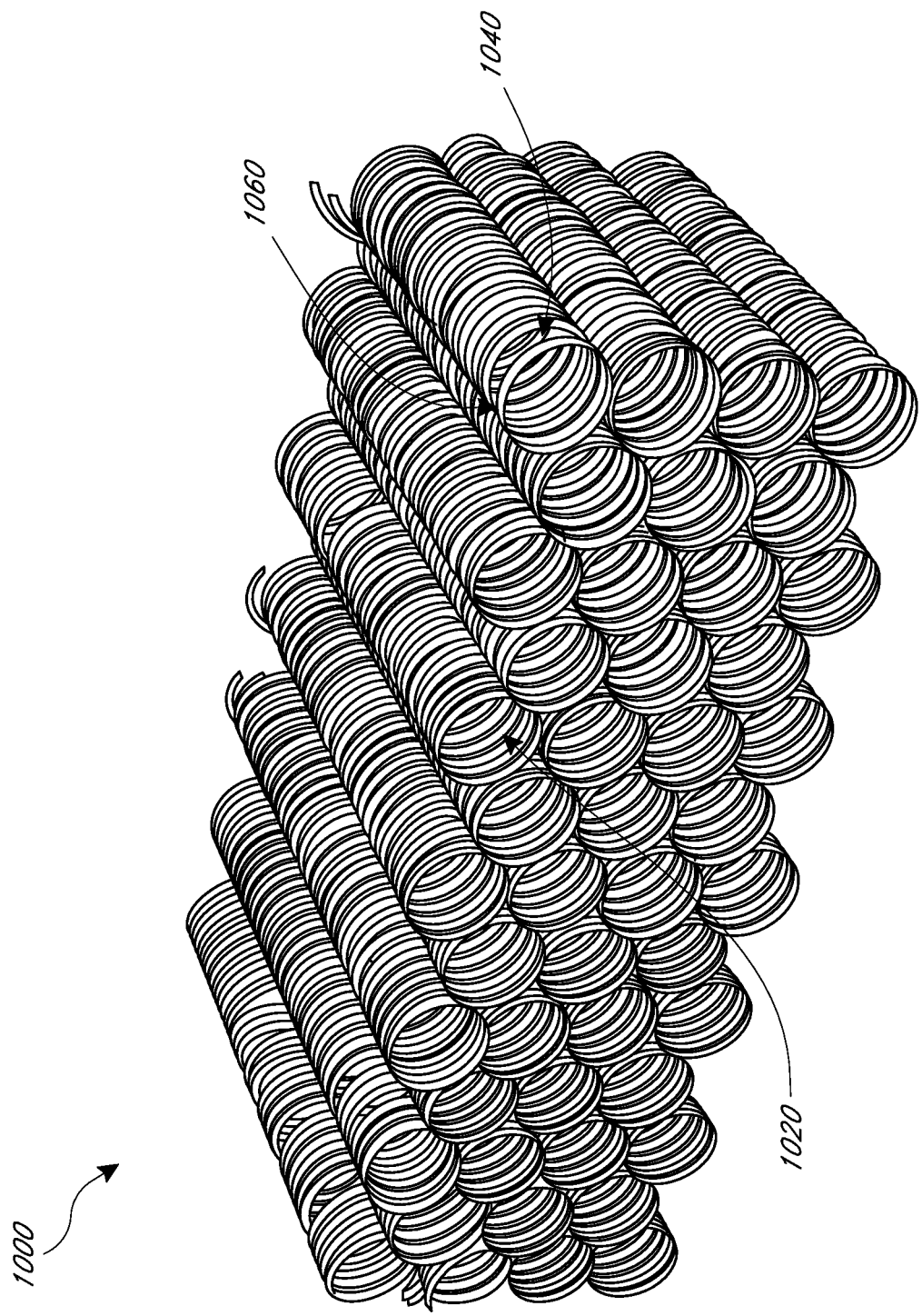

Corrugated unit 450 can be used as a wound packing without further modification. It can also be used to form more complex three-dimensional structures. Spiral wound packing 500 illustrated in FIGS. 15B and 15C is formed by rolling corrugated unit 450 to expose a portion of the first flat sheet 410 along the circumference. More elaborate structures can also be formed from a plurality of corrugated units. For example, individual corrugated units may be coupled to each other by adhesive or heat sealing means to form multi-corrugated wound packing 550, as shown in FIG. 15D. One or more beads of silicone material 552 can serve dual purposes of coupling the corrugated units 450, and improving the resiliency of the structure. It should be noted that, while FIG. 15D illustrates this embodiment with the peaks of each adjacent corrugation unit in alignment, a staggered configuration is also contemplated. Multi-corrugated wound packing 550 can also be sliced along a cross section at a suitable thickness to produce cut corrugated wound packing. Alternatively, wound packing 550 can be sliced at a bias to produce biased-cut corrugated Wound packing.

Spiral wound packing 500, cut corrugated wound packing, and biased-cut corrugated wound packing have the benefit of being highly compressible and highly resilient. Preferably, these wound packing structures are sufficiently compressible to reduce to less than 50% of their original volume when subjected to the approximately 2 psi (pounds per square inch) compression force commonly encountered with the application of suction. More preferably, the wound packing is sufficiently compressible to reduce to less than 25% of its original volume. Most preferably, the wound packing is sufficiently compressible to reduce to less than 10% of its original volume.

Figure 15E:
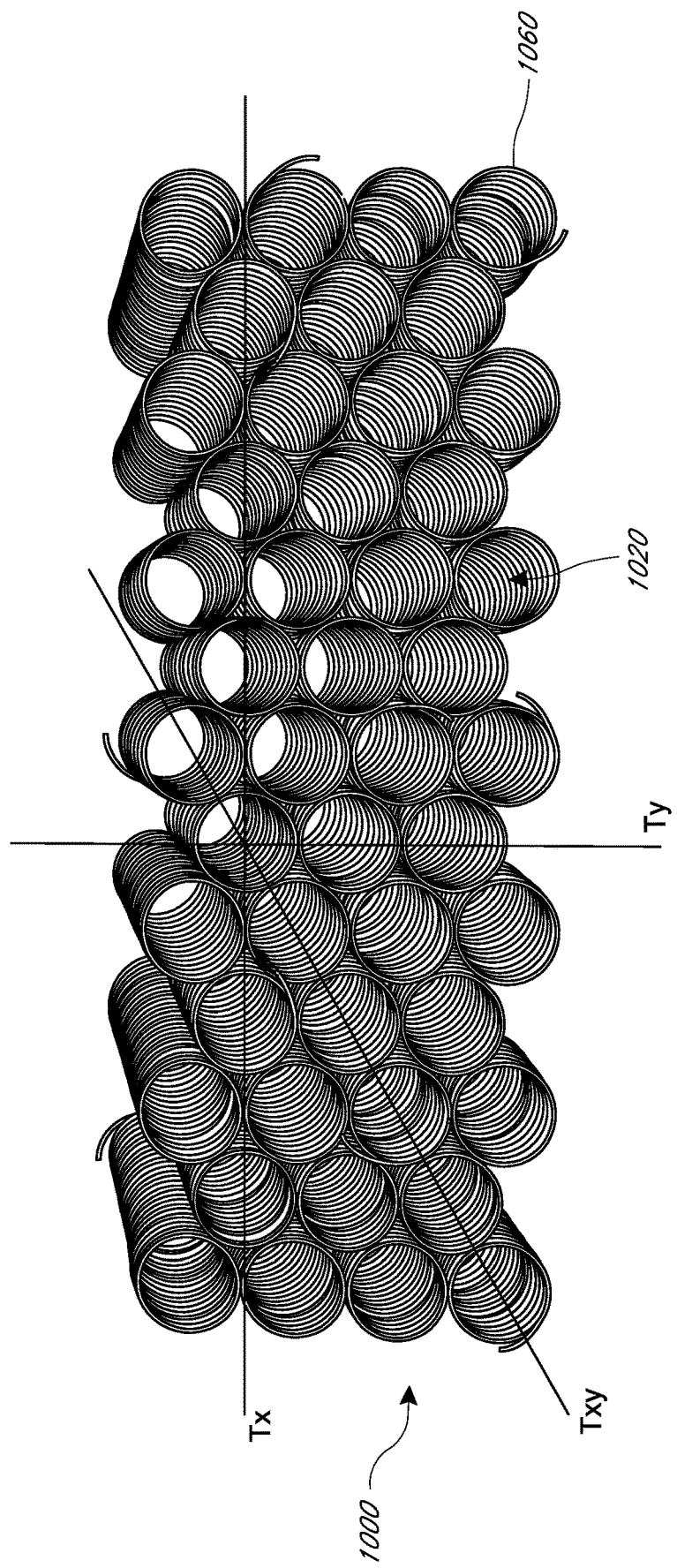
Figure 15F:
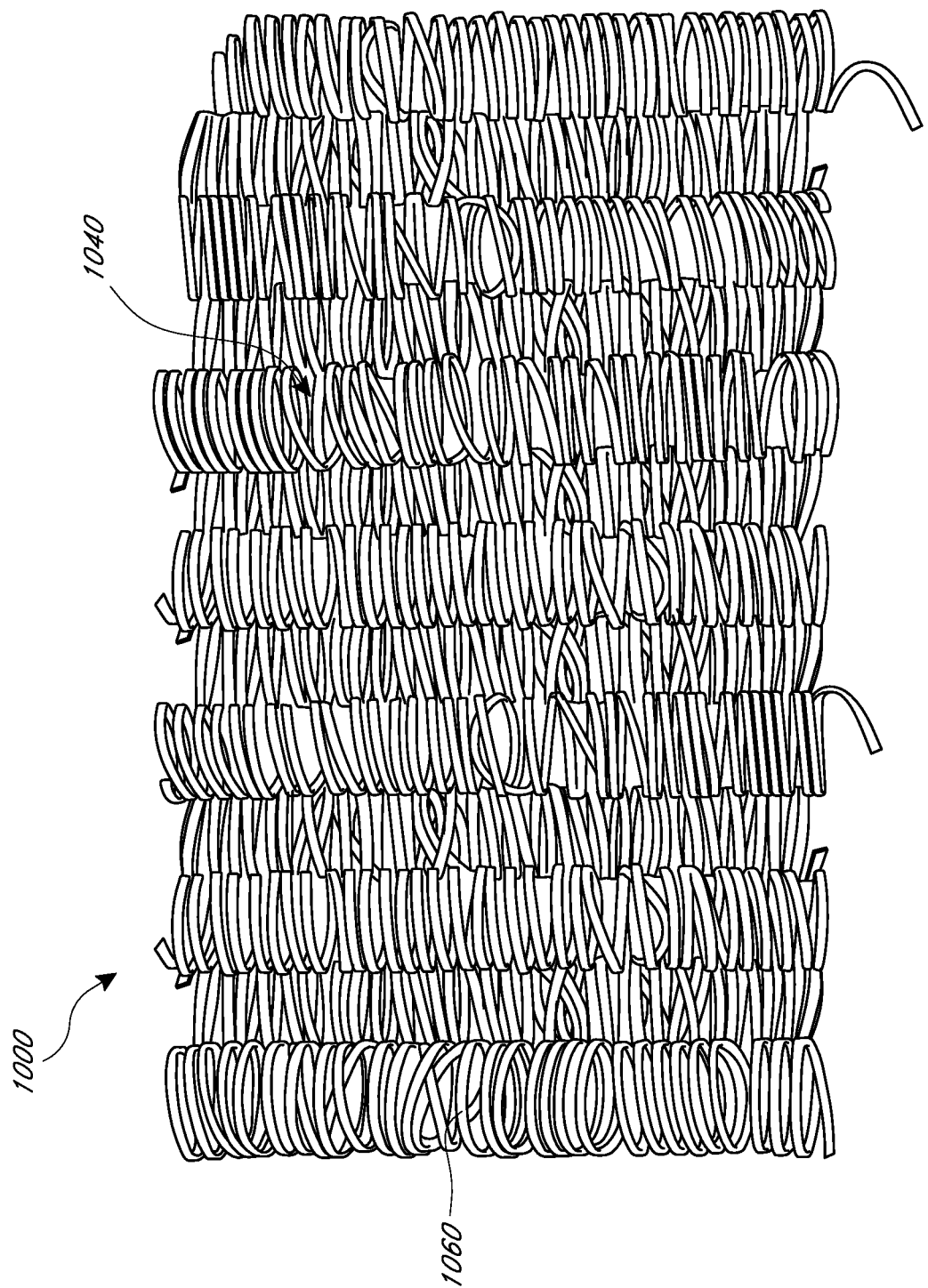

FIGS. 15D-15F illustrate another embodiment of a wound filler. As shown in FIG. 15D, wound packing material 1000 has a generally spiral shape exhibiting open areas 1020 along the longitudinal axis of the fiber spiral and open areas 1040 between adjacent segments of a particular spiral. Wound packing material 1000 is generally constructed from polymer fibers 1060, such as spandex.

To form wound packing material 1000, fibers 1060 are wrapped around mandrels, such as a steel tube (not shown). The steel tubes with the spandex wrap are stacked in rows and a polyurethane film (not shown) is placed between each row. Desirably, the polyurethane film is about 0.003 inch thick. The stack of tubes is then clamped together and heated to about 320 degrees F. The polyurethane film melts and adheres to the spandex fibers, thus coupling the adjacent spirals to one another. After cooling, the steel tubes are removed. Wound packing material 1000, as illustrated in FIGS. 15D-15F, remains.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A system for providing negative pressure wound therapy to a wound, comprising:
   a backing layer for providing a substantially air and liquid-tight seal over a wound cavity;
   a first pressure sensor for detecting pressure within the wound cavity, the first pressure sensor positioned inside a bladder member within the wound cavity, wherein the bladder member comprises a structural member inside the bladder member and the structural member is configured to be more rigid in a vertical direction than in a lateral direction;
   a source of negative pressure for providing negative pressure to a space beneath the backing layer;
   a canister configured to collect wound exudate removed from the wound;
   a second pressure sensor positioned in the fluid path between the dressing and the source for negative pressure; and
   a controller programmed to receive sensor data from the first and second pressure sensor and control the negative pressure provided based on the sensor data.

2. The system of claim 1, further comprising a wound packing member or wound filler.

3. The system of claim 2, wherein the wound packing member or wound filler comprises a sealed member that can be controllably inflatable and deflatable from a pressure source.

4. The system of claim 3, further comprising a pump configured to control a level of pressure within the sealed member.

5. The system of claim 2, further comprising an organ protection layer configured to be positioned between the wound packing member or wound filler and the viscera or other organs.

6. The system of claim 1, further comprising a third pressure sensor for measuring internal abdominal pressure, wherein the third pressure sensor is configured to be placed in communication with a human organ.

7. The system of claim 1, wherein the wound is an abdominal wound.

8. The system of claim 1, wherein the wound is a wound on a limb.

* * * * *